(12) United States Patent
Clauss et al.

(10) Patent No.: US 8,486,405 B2
(45) Date of Patent: Jul. 16, 2013

(54) METHOD FOR DIAGNOSING AND TREATING EMPHYSEMA

(75) Inventors: Matthias Clauss, Indianapolis, IN (US); Irina Petrache, Indianapolis, IN (US); Robert Voswinckel, Giessen (DE)

(73) Assignee: Indiana University Research and Technology Corp., Indianapolis, IN (US)

( * ) Notice: Subject to any disclaimer, the term of this patent is extended or adjusted under 35 U.S.C. 154(b) by 0 days.

(21) Appl. No.: 13/309,479

(22) Filed: Dec. 1, 2011

(65) Prior Publication Data

US 2012/0195906 A1 Aug. 2, 2012

Related U.S. Application Data

(62) Division of application No. 12/933,278, filed as application No. PCT/US2009/037842 on Mar. 20, 2009, now abandoned.

(60) Provisional application No. 61/038,342, filed on Mar. 20, 2008, provisional application No. 61/111,729, filed on Nov. 6, 2008.

(51) Int. Cl.
*A61K 39/395* (2006.01)
*C07K 16/24* (2006.01)

(52) U.S. Cl.
USPC .................................. 424/145.1; 530/388.23

(58) Field of Classification Search
None
See application file for complete search history.

(56) References Cited

U.S. PATENT DOCUMENTS

| | | | |
|---|---|---|---|
| 5,641,867 A | 6/1997 | Stern et al. | |
| 6,184,358 B1 | 2/2001 | Loetscher et al. | |
| 6,723,055 B2 | 4/2004 | Hoffman | |
| 7,264,803 B2 | 9/2007 | Schwarz | |
| 2003/0039652 A1* | 2/2003 | Schwarz | 424/146.1 |
| 2010/0047238 A1 | 2/2010 | Smith | |

FOREIGN PATENT DOCUMENTS

WO  WO 2009/094168   7/2009

OTHER PUBLICATIONS

International Searching Authority, International Search Report for PCT/US2009/037842, issued Nov. 2009.
International Searching Authority, Written Opinion for PCT/US2009/03784, issued Nov. 2009.
International Searching Authority, International Preliminary Report on Patentability for PCT/US2009/03784, issued Sep. 2010.
Journeay, W.S., "Pulmonary Toxicity Studies on Self-assembling Rosette Nanotubes." University of Saskatchewan Library Electronic Theses & dissertation, 2007.
Clauss, M, et al., "EMAP II Overexpression Induces Endothelial Apotptosis and Emphysema in Murine Lungs." The FASEB Journal, Apr. 2008, vol. 22, Meeting Abstract 47.9.
Voswinckel, R., et al, "Circulating Vascular Progenitor Cells Do Not Contribute to Compensatory lung Growth," Circulation Research, vol. 93: Jul. 2003.
Rajashekhar, G., et al, "A monoclonal rat anti-mouse EMAP II antibody that functionally neutralizes pro- and mature—EMAP II in vitro," Journal of Immunological Methods, 350, p. 2228, Aug. 2009.
Hycult Biotech, Product description and specifications for EMAPII, Mouse, mAB M7/1, available at http://www.hycultbiotech.com/chemo-cytokines-antibodies-emapii-mouse-mab-m7-1-p11756-html, downloaded Jan. 28, 2013.
EMB Millipore Corp., Product information for Anti-EMAPII Antibody, clone M7/1, (Preservative free), available at http://www.millipore.com/catalogue/item/mabs278, downloaded Jan. 28, 2013.
GenBank Accession No. NP_001495 [online[, National Center for Biotechnology Information, Bethesda, MD., Jun. 19, 20011 [retrieved from the internet of Jan. 28, 2013, URL: http://www.ncbi.nlm.nih.gov/protein/NP_001495].
Clauss, M., et al., "Lung endothelial monocyte-activating protein 2 is a mediator of cigarette smoke-induced emphysema in mice" Journal of Clinical Investigation, vol. 121, No. 6, Jun. 2011, p. 2470-2479.

* cited by examiner

*Primary Examiner* — David Romeo
(74) *Attorney, Agent, or Firm* — Faegre Baker Daniels LLP

(57) ABSTRACT

The present invention provides methods for diagnosing a patient with emphysema or COPD by detecting the levels of EMAP II in a sample. Alternatively, methods are provided for determining the susceptibility of a patient to develop emphysema or COPD by detecting the levels of EMAP II in a sample. The levels of EMAP II may be determined by immunoassay techniques. The present invention also provides methods for treating patients with emphysema or COPD by administering a therapeutically effective amount of an EMAP II neutralizing compound. The compound may be an antibody, siRNA, antisense RNA or an antagonist of CXCR3.

1 Claim, 23 Drawing Sheets

FIGURE 2A
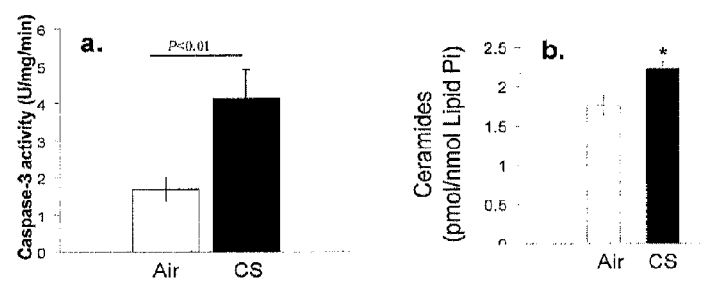
FIGURE 2B
FIGURE 2C
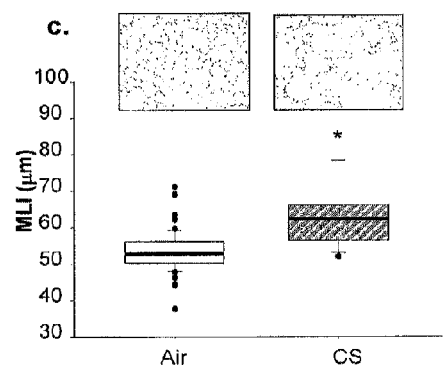

FIGURE 3A
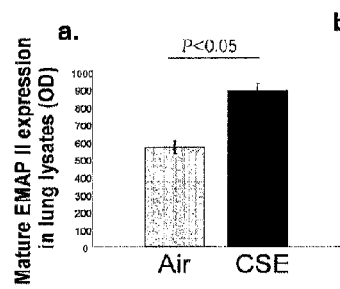
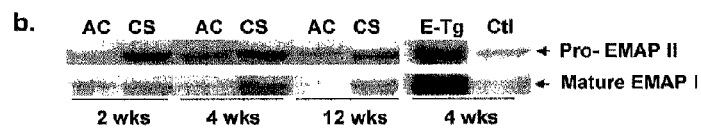
FIGURE 3B
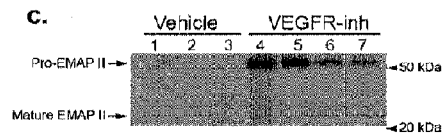
FIGURE 3C

METHOD FOR DIAGNOSING AND TREATING EMPHYSEMA

CROSS REFERENCE TO RELATED APPLICATIONS

This application is a divisional of U.S. patent application Ser. No. 12/933,278, entitled METHOD FOR DIAGNOSING AND TREATING EMPHYSEMA, filed on Feb. 25, 2011, which is a National Stage filing of International Application Serial No. PCT/US2009/037842, entitled, "METHOD FOR DIAGNOSING AND TREATING EMPHYSEMA" which claims the benefit under 35, U.S.C. §119(e) of U.S. Provisional Patent Application Ser. Nos. 61/038,342, filed Mar. 20, 2008, and 61/111,729, filed Nov. 6, 2008, the disclosures of which are each expressly incorporated herein by reference in their entirety.

BACKGROUND OF THE INVENTION

The present invention is directed generally to method for diagnosing and treating a patient with emphysema or COPD and more particularly to methods for diagnosing and treating a patient with emphysema or COPD by detecting the presence of EMAP II and neutralizing EMAP II.

Over 3.1 million Americans have been diagnosed with emphysema. Emphysema and chronic bronchitis are the two components of the syndrome of chronic obstructive pulmonary disease (COPD). COPD is the fourth leading cause of death in America. (See www.nhlbi.nih.gov/health/public/lung/other/copd_fact.htm#toc). This disease has no effective treatment that reverses its course or halts its progression.

Pulmonary emphysema is a prevalent fatal disease, characterized by loss of both matrix and cellular elements of the lung, thus impairing gas exchange between the alveolar space and the capillary blood. Emphysema is defined as "a condition of the lung characterized by abnormal, permanent enlargement of airspaces distal to the terminal bronchiole, accompanied by destruction of their walls, with or without obvious fibrosis". Report of a National Heart, Lung, and Blood Institute, Division of Lung Diseases workshop, *Am Rev Respir Dis* 132, 182-185. (1985). The concepts of permanent and destruction are critical in this definition as they convey the unique and characteristic distinguishing features of a disease process ultimately leading to the disappearance of lung tissue.

Although the environmental inducers in susceptible individuals have been identified, the mechanisms by which these initiate a loss of alveoli leading to emphysema are poorly understood. Over the past decades, inflammation and a protease/antiprotease imbalance have been proposed to act as downstream effectors of the lung destruction following chronic cigarette smoking, which accounts for most cases of emphysema. Pro-inflammatory stimuli are postulated to recruit and activate lung inflammatory cells, triggering matrix protease release and lung remodeling. Shapiro, S. D., *J Clin Invest* 106, 1309-1310 (2000). However, these models fail to fully account for the mechanisms behind the eradication of septal structures and the unique nature of lung destruction as compared to alterations seen in other inflammatory lung diseases. To account for the permanent destruction seen in emphysema, excessive apoptosis of structural alveolar cells have emerged as a second major mechanism of emphysema. Excessive alveolar endothelial apoptosis is thought to cause capillary regression, with subsequent loss of alveolar wall. Tuder, R. M. et al., *Am J Respir Cell Mol Biol* 28, 551-554 (2003). However, the coexistence of an excessive lung structural cell apoptosis with that of an activated inflammatory state in emphysema and the hierarchy of these two mechanisms have not yet been explained.

As can be seen, there is a need for a method for treating pulmonary emphysema. There is also a need for a method for diagnosing pulmonary emphysema in the early stages. Early diagnosis and subsequent treatment may result in more effective treatment of the disease and a better prognosis for the patient.

SUMMARY OF THE INVENTION

In one aspect of the present invention there is provided a method of diagnosing a patient for emphysema or COPD comprising detecting the overexpression of EMAP II in a patient's biological sample where the sample may be serum, plasma, lung lavage or lung biopsy. The EMAP II may be detected by immunological methods such as ELISA, sandwich ELISA or western blot. The overexpression of EMAP II may be determined by comparing to a control sample.

In another aspect of the present invention there is provided a method of predicting a patient's susceptibility of developing emphysema or COPD by detecting the presence of EMAP II in a patient's sample.

In a further aspect of the present invention there is provided a method for treating a patient having emphysema or COPD comprising administering a therapeutically effective amount of an EMAP II neutralizing compound. The EMAP II neutralizing compound may be an antibody, an agonist of the CXCR3 receptor, an siRNA or antisense RNA. The EMAP II neutralizing compound may be administered systemically or by inhalation.

These and other features, aspects and advantages of the present invention will become better understood with reference to the following drawings, description and claims.

BRIEF DESCRIPTION OF THE DRAWINGS

FIG. 2A is a bar graph showing the effect of cigarette smoke exposure on the activity levels of caspase-3 in mouse lung;

FIG. 2B is a bar graph showing the effect of cigarette smoke on the levels of pro-apoptotic ceramide levels in mouse lungs;

FIG. 2C shows the alveolar size in mice exposed to cigarette smoke for 6 months;

FIG. 3A is a bar graph showing the effect of cigarette smoke exposure on the levels of EMAP II expression;

FIG. 3B is a western blot showing the kinetics of EMAP II secretion in bronchoalveolar lavage from mice exposed to cigarette smoke (CS) or air (AC);

FIG. 3C is a western blot showing VEGF receptor inhibition with SU5416;

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
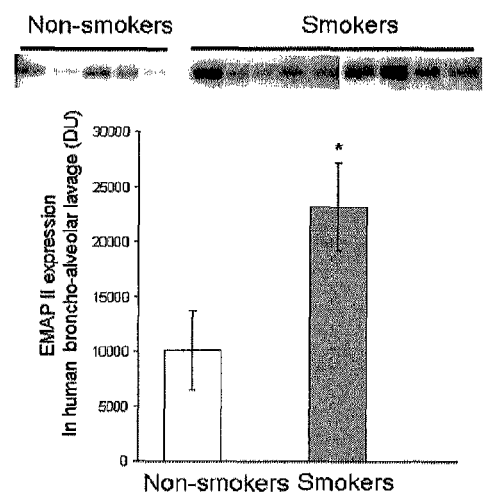
FIG. 1 shows the increase in secreted EMAP II expression in humans in the broncho-alveolar lavage (BAL) of smokers compared to non-smokers.

Broadly, the present invention provides methods for diagnosing or treating a patient with emphysema or COPD comprising detecting the presence of endothelial monocyte activating protein II (EMAP II) in a biological sample from a patient or treating with a therapeutically effective amount of an EMAP II neutralizing compound. The same method may also be used to determine if a patient is susceptible to developing emphysema of COPD. EMAP II is a cytokine induced by conditions present in emphysematous lungs including oxidative, apoptotic, and hypoxic cellular stresses. EMAP II is released from cells as either a 43 kD pro-form or a 23 kDa "mature" protein upon proteolytic cleavage by proteases including caspases and matrix metalloproteinases (MMPs), which are known to participate in COPD. Given the potent pro-apoptotic effect of EMAP II on lung endothelial cells, coupled with its ability to recruit pro-inflammatory monocytes, excessive EMAP II release in response to cigarette smoking may engage both lung endothelial cell apoptosis and accumulation of lung macrophages, and therefore may be a key molecular mediator of pulmonary emphysema. It has now been discovered by the inventors that smoke-induced emphysema is preceded by robust EMAP II production and apoptosis in mice and that lung-specific increases in EMAP II are sufficient to cause lung apoptosis and emphysema. Moreover, increased levels of EMAP II have now been measured in the lungs of emphysema patients and EMAP II has been found to be robustly upregulated in the bronchoalveolar lavage of smokers (FIG. 1). Therefore, EMAP II may be a biomarker for emphysema and COPD, allowing for earlier detection and treatment of these conditions.

In one embodiment a method is provided for diagnosing whether or not a patient has emphysema or COD where the method may comprise the step of detecting EMAP II in a biological sample from a patient. It has been found that expression of EMAP II is significantly elevated by at least 2-fold in samples from patients who have emphysema or COPD. The method may further comprise comparing the EMAP II detected in the patient's sample with a control and diagnosing the patient as either having emphysema or COPD. The control may be a sample from a patient who does not have emphysema or COPD and more specifically, from a patient who does not smoke. Control levels of EMAP II may be defined by a number of samples from control patients wherein the expression levels of EMAP II. It will be appreciated that the more control samples available, the better the comparison. The comparison may be a visual comparison observing elevated EMAP II levels or the amount of EMAP II in the sample and/or control may be quantified and then compared.

In one embodiment, the biological sample may be serum, plasma, bronchoaveolar lavage or lung biopsy. Obtaining such samples is routine in the art. The overexpression of EMAP II in a biological sample may be assessed at the protein or nucleic acid level. In an illustrative embodiment, immunocytochemistry techniques are provided that utilize antibodies to detect the overexpression EMAP II in biological samples. In this aspect of the invention, at least one antibody directed to EMAP II may be used. Overexpression of EMAP II may also be detected by nucleic acid-based techniques, including, for example, hybridization and RT-PCR. Kits comprising reagents for practicing the methods of the invention are further provided.

Methods for detecting EMAP II may comprise any methods that determine the quantity or the presence of EMAP II either at the nucleic acid or protein level. Such methods are well known in the art and include but are not limited to western blots, northern blots, southern blots, ELISA, immunoprecipitation, immunofluorescence, flow cytometry, immunocytochemistry, nucleic acid hybridization techniques, nucleic acid reverse transcription methods, and nucleic acid amplification methods. In illustrative embodiments, overexpression of a EMAP II may be detected on a protein level using, for example, antibodies that are directed against specific biomarker proteins. The antibodies may be, but not limited to, polyclonal and monoclonal antibodies. Examples of monoclonal antibodies are provided herein as well as in U.S. Pat. No. 5,641,867, incorporated by reference herein. These antibodies can be used in various methods such as Western blot, ELISA, immunoprecipitation, or immunocytochemistry techniques.

In one embodiment, EMAP II overexpression may be determined on the protein level. Antibodies specific for EMAP II may be utilized to detect the overexpression of a biomarker protein in a body sample. The method comprises obtaining a body sample from a patient, contacting the body sample with at least one antibody directed to EMAP II, and detecting antibody binding to determine if EMAP II is overexpressed in the patient sample. Overexpression of EMAP II may be determined by comparing the results to a control sample.

In an alternate embodiment, EMAP II overexpression may be detected at the nucleic acid level. Nucleic acid-based techniques for assessing expression are well known in the art and include, for example, determining the level of biomarker mRNA in a body sample. Many expression detection methods use isolated RNA. Any RNA isolation technique that does not select against the isolation of mRNA can be utilized for the purification of RNA from cervical cells (see, e.g., Ausubel et al., ed., (1987-1999) Current Protocols in Molecular Biology (John Wiley & Sons, New York). Additionally, large numbers of tissue samples can readily be processed using techniques well known to those of skill in the art, such as, for example, the single-step RNA isolation process of U.S. Pat. No. 4,843, 155, incorporated by reference herein.

Isolated mRNA may be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe may be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker of the present invention. The polynucleotide sequence of EMAP II is known in the art (i.e. U.S. Pat. No. 6,013,483, incorporated by reference herein) and nucleic acid probes may be selected without undue experimentation. Hybridization of an mRNA with the probe indicates that the biomarker in question is being expressed.

In another embodiment methods are provided for determining a patient's susceptibility to developing emphysema or COPD. Although no symptoms may be present, those who smoke or were habitual smokers in the past have a significantly higher risk of developing emphysema than those who never smoked. Therefore, it may be desirable to determine the susceptibility of a patient who is a smoker to develop emphysema. Early detection may lead to a better treatment regime. The method may comprise the step of detecting EMAP II in a patient's sample as described above. The method may further comprise comparing the EMAP II in the patient's sample with a control as described above.

In yet another embodiment, kits for practicing the methods of the present invention are further provided. The kit may comprise at least one reagent, e.g., an antibody, a nucleic acid probe, etc. for specifically detecting the expression of EMAP II. The kits may also comprise positive and/or negative controls to validate the activity and correct usage of reagents employed in accordance with the invention. Controls may include biological samples, such as lung tissue or lung lavage samples from control patients (negative control). EMAP II may be added to the control samples to provide positive controls.

In a further embodiment methods are provided for treating a patient having emphysema or COPD comprising the step of administering a therapeutically effective amount of at least one EMAP II neutralizing compound. The neutralizing compound may be any compound or molecule that decreases or inhibits the activity or action of EMAP II in the patient. In one embodiment the neutralizing compound may be an anti-EMAP II antibody where the antibody may be a polyclonal or monoclonal antibody, antibody fragments, humanized or chimeric antibodies that retain the combining region that specifically binds to EMAP II.

In an alternate embodiment the neutralizing compound may be an agonist of the CXCR3 receptor. The agonist may be a peptide, peptidomimetic or any other compound that disrupts the interaction between EMAP II and the CXCR3 receptor. In an illustrative embodiment, the neutralizing compound is an EMAP II analog. Interruption of the binding of EMAP II to CXCR3 may interfere with the detrimental action of EMAP II in lung tissue.

Figure 9:
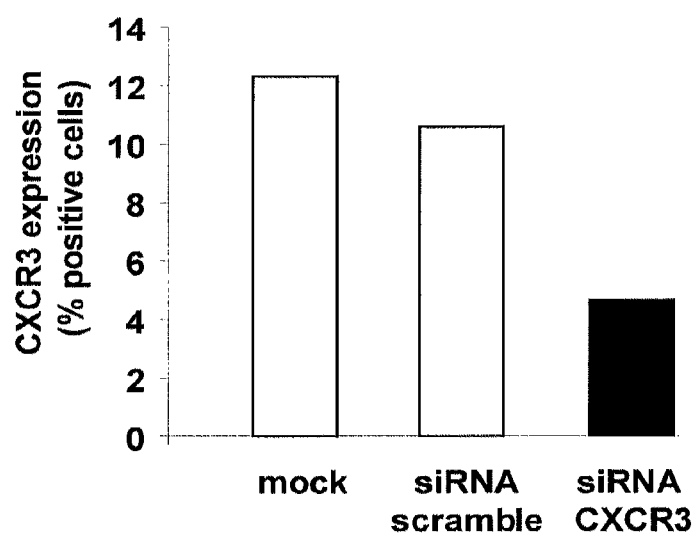
FIG. 9 is a bar graph showing the effect of CXCR3-targeting siRNA on CXCR3 expression.

In yet another embodiment, the neutralizing compound may be a compound or molecule that decreases the expression of EMAP II. Non-limiting examples may be siRNA or antisense RNA targeted to EMAP II RNA or DNA. Alternatively, the neutralizing compound may be a compound or molecule such as, but not limited to, siRNA or antisense RNA, that interferes and decreases the expression of CXCR3. As shown in FIG. 9, when human lung microvascular endothelial cells were electroporated in the presence of CXCR3-targeting siRNA, CXCR3 expression levels showed reductions of about 60% to about 80%. As the nucleotide sequences are known for both EMAP II and CXCR3, one skilled in the art would be able to select siRNA and/or antisense RNA sequences for EMAP II and/or CXCR3 without undue experimentation. Examples of compounds and compositions for modulating the expression of EMAP II are disclosed in U.S. Patent Application Publication No. 2004/0110114 and U.S. Pat. No. 5,665,593, both expressly incorporated by reference herein.

In one embodiment, protocols for the administration of the EMAP II neutralizing compounds are similar to the protocols for the administration of any other agent typically administered for a lung disorder. As a general guideline, protocols developed for the administration of any agent for the treatment of lung disease form a starting point for the administration of the EMAP II neutralizing compounds of the present invention. Thus, the EMAP II neutralizing compounds and compositions are administered via an inhalant or any other mechanism by which a disorder such as asthma is treated. In one embodiment of the invention, the active compounds or pharmaceutical formulations of the invention are administered directly to the lungs of the subject by any suitable means, but are preferably administered by administering an aerosol suspension of respirable particles comprised of the active compound, which the subject inhales. The active compound can be aerosolized in a variety of forms, such as, but not limited to, dry powder inhalants, metered dose inhalants, or liquid/liquid suspensions. The respirable particles may be liquid or solid. Alternatively, EMAP II neutralizing compounds may be administered systemically, either intravenously or through other means known in the art.

Any of the protocols, formulations, routes of administration and the like that have previously been used in the treatment of lung disorders may readily be modified for use in the present invention. In some cases, mechanical ventilation is appropriate. Such ventilation may include high-frequency oscillatory ventilation (HFOV) or other unconventional forms of mechanical ventilation. Theoretically, partial liquid ventilation (PLV) offers the advantage of lung lavage combined with ventilator support.

In another embodiment, the dosages are determined using an animal model, such as the EMAP II double transgenic models known to those of skill in the art, and modified and adapted to use in higher mammals. The total dose of therapeutic agent is administered in multiple doses or in a single dose. In certain embodiments, the compositions are administered alone, in other embodiments the compositions are administered in conjunction with other therapeutics directed to the disease or directed to other symptoms thereof.

Regardless of the route of administration of the active compounds or formulations of the invention, the therapeutically effective dosage of any one active compound, the use of which is in the scope of present invention, will vary somewhat from compound to compound, and patient to patient, and will depend upon factors such as the age, weight and condition of the patient, and the route of delivery. Such dosages can be determined in accordance with routine pharmacological procedures known to those skilled in the art. In one exemplary embodiment, a dosage from about 0.1 to about 50 mg/kg will have therapeutic efficacy, with all weights being calculated based upon the weight of the active compound. Toxicity concerns at the higher level may restrict intravenous dosages to a lower level such as up to about 10 mg/kg. A dosage from about 10 mg/kg to about 50 mg/kg may be employed for oral administration. Typically, a dosage from about 0.5 mg/kg to 5 mg/kg may be employed for intramuscular injection. Preferred dosages are 1 µmol/kg to 50 µmol/kg, and more preferably 22 µmol/kg and 33 µmol/kg of the compound for intravenous or oral administration.

In another exemplary embodiment, dosages of the compounds of the present invention, for antisense oligonucleotides the dosage is preferably one which produces intracellular concentrations of the oligonucleotide of from 0.05 to 50 µM. Typically the dosage to a human will be from about 0.01, 0.1 or 1 mg/Kg up to 50, 100, or 150 mg/Kg. In an additional example, for antibodies the dosage is typically 0.01, 0.05 or 0.1 mg/Kg up to 20, 40 or 60 mg/Kg.

When administration of the active compounds or pharmaceutical formulations is via inhalation, the dosage of active compound will also vary depending on the condition being treated and the state of the subject, but generally may be an amount sufficient to achieve dissolved concentrations of active compound on the airway surfaces of the subject of from about $10^{-9}$ to about $10^{-1}$ Moles/liter, and more preferably from about $10^{-6}$ to about $10^{-4}$ Moles/liter.

Methods of formulating antibodies, peptides or other compounds for therapeutic administration are known to those of skill in the art. Methods of formulating siRNA or antisense RNA are also known in the art. Administration of these compositions according to the present invention will be via any common route so long as the target tissue is available via that route. Most commonly, these compositions are formulated for oral administration, such as by an inhalant. However, other conventional routes of administration, e.g., by subcutaneous, intravenous, intradermal, intramusclar, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site also is used particularly when oral administration is problematic. The treatment may consist of a single dose or a plurality of doses over a period of time.

It will be appreciated by those skilled in the art that the compounds of the present invention can be employed in a wide variety of pharmaceutical forms; the compound can be employed neat or admixed with a pharmaceutically acceptable carrier or other excipients or additives. Generally speaking, the compound will be administered orally or intravenously. It will be appreciated that therapeutically acceptable salts of the compounds of the present invention may also be employed. The selection of dosage, rate/frequency and means of administration is well within the skill of the artisan and may be left to the judgment of the treating physician. The method of the present invention may be employed alone or in conjunction with other therapeutic regimens.

Upon formulation, solutions will be administered in a manner compatible with the dosage formulation and in such amount as is therapeutically effective. The formulations are easily administered in a variety of dosage forms such as inhalents, injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration.

The frequency of dosing will depend on the pharmacokinetic parameters of the agents and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, bodyweight, sex and diet of the patient, the severity of any infection, time of administration and other clinical factors. As studies are conducted, further information will emerge regarding appropriate dosage levels and duration of treatment for specific diseases and conditions.

In one embodiment of the present invention methods are provided for monitoring the effectiveness of treatment of a patient for emphysema and/or COPD and undergoing treatment by determining the expression levels of EMAP II. The method may comprise the step of detecting EMAP II in a patient's sample as described above. The method may further comprise comparing the EMAP II in the patient's sample with a control as described above. Alternatively, the EMAP II expression levels may be compared to a sample from the same patient before treatment (i.e. from diagnosis) and/or samples from earlier in the treatment. In an illustrative embodiment, a method is provided comprising the steps of diagnosing a patient for emphysema and/or COPD by determining the expression level of EMAP II, treating the patient if the diagnosis was positive and monitoring the effectiveness of the treatment by determining the expression level of EMAP II during the treatment.

EXAMPLE 1

Methods

Reagents and antibodies. All chemical reagents were purchased from Sigma-Aldrich (St. Louis, Mo.), unless otherwise stated. EMAP II antiserum was produced as recently described (Knies, U. E., Kroger, S., and Clauss, M. 2000. Expression of EMAP II in the developing and adult mouse. *Apoptosis* 5:141-151). Other antibodies employed were of commercial source, including MAC-3 (Becton Dickinson Biosciences, Franklin Lakes, N.J.), CXCR3 (R&D systems, Minneapolis, Minn.), and MMP-12 (R&D).

Cells. Human lung microvascular endothelial cells (HLMVEC) were obtained from Lonza (Allendale, N.J.) and maintained in culture medium consisting of EMB-2, 10% FBS, 0.4% hydrocortisone, 1.6% hFGF, 1% VEGF, 1% IGF-1, 1% ascorbic acid, 1% hEGF, 1% GA-100, and 1% heparin. All primary cell cultures were maintained at 37° C. in 5% $CO_2$ and 95% air. Experiments were performed up to passage 10 with cells at 80-100% confluence.

Monoclonal anti-EMAP II antibody. The rat monoclonal neutralizing antibody M7 against mouse EMAP II was developed by immunizing Lewis rats with recombinant murine pro-EMAP II. Lymphocytes isolated from the spleen and lymph nodes of immunized rats were fused with the mouse myeloma SP2/0, and Clones were selected by testing hybridoma supernatants in enzyme-linked immunosorbent assays (ELISAs) for binding both pro- and mature EMAP II . The clones most active in ELSIA were further characterized by Western blotting and neutralization of EMAP II-induced endothelial apoptosis in tissue culture experiments (manuscript in preparation). For purification of MoAbs for in vivo studies, hybridomas were grown in protein-free hybridoma medium (GIBCO-BRL) and antibodies were purified with protein G-Sepharose (Pharmacia, Uppsala, Sweden).

Animal studies. C57/BI6 mice were purchased from Jacksons Lab. A lung-specific inducible EMAP II transgenic mouse was generated by crossing the EMAP II responder mouse with homozygous transgenic mice containing the transactivator controlled by the lung epithelium specific CCSP. The EMAP II responder transgenic mouse contained the secreted (mature) form of EMAP II under a minimal promoter containing tetracycline-inducible sequences. Therefore the murine mature EMAP II cloned from meth mouse tumor cells (Knies, U. E., Behrensdorf, H. A., Mitchell, C. A., Deutsch, U., Risau, W., Drexler, H. C., and Clauss, M. 1998. Regulation of endothelial monocyte-activating polypeptide II release by apoptosis. *Proc Natl Acad Sci USA* 95:12322-12327) and fused to a signal peptide derived from INFb was inserted into the tet-repeat containing plasmid pUD10-3 by using Sac II and a Xho I insertion sites. The resulting plasmid was injected into oocytes for implantation into foster mice and a transgenic line was established. After crossing of the resulting responder mice with the rtTA transactivator mice, the first generation of mice heterozygous for the EMAP II responder transgene were compared to the CCSP transactivator with CCSP transactivator-only transgenic mice. Of note, only the EMAP II/CCSP transactivator but not the CCSP transactivator-only transgene can induce EMAP II expression. With this design, CCSP transactivator background effects and tetracycline effects can be ruled out, as both groups can be treated with tetracycline. Transgenic mice were bred in an AAALAC accredited animal facility. Double transgenic EMAP II/CCSP-rtTA and single transgenic CCSP-rtTA mice were maintained on regular water until 3 to 4 month of age. Thereafter, the mice were placed on doxycycline treatment for up to 6 months. At the end of experiments, the mice were euthanized and the tissue was processed as described (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). In addition, mice underwent bronchoalveolar lavage (BAL) with 0.6 ml of PBS thrice. BAL cells were sedimented via centrifugation and the acellular fluid was then snap-frozen in liquid nitrogen and stored at −80° C. for further analysis.

Cigarette smoke exposure. Cigarette smoke exposure was performed as previously described (Cavarra, E., Bartalesi, B., Lucattelli, M., Fineschi, S., Lunghi, B., Gambelli, F., Ortiz, L. A., Martorana, P. A., and Lungarella, G. 2001. Effects of cigarette smoke in mice with different levels of alpha(1)-proteinase inhibitor and sensitivity to oxidants. *Am J Respir Crit Care Med* 164:886-890). Mice (C57/BI6 mice, female, age 12 weeks; n=5-10 per group) were exposed to cigarette smoke or ambient air for up to 24 weeks. In a separate experiment, double transgenic EMAP II/CCSP transactivator or single transgenic CCSP transactivator control littermates, male and female, age 12 weeks; n=5-10 per group were exposed to cigarette smoke or ambient air by a similar protocol as above. Prior to (for the duration indicated) and during the cigarette smoke exposure, all transgenic mice received water with doxycycline. In a separate experiment, mice (DBA2, female, age 12 weeks; n=5-12 per group) were exposed to cigarette smoke as described above or ambient air for four months; during the third month of cigarette smoke exposure, two groups of mice exposed to cigarette smoke received either EMAP II antibody by nebulization or isotype IgG control, and one group exposed to ambient air received isotype IgG control. The day following the end of the cigarette smoking schedule in all experiments mice were euthanized and lung processing was performed as previously described (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498).

VEGF receptor blockade: VEGF receptor blockade was performed as previously described (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). Mice (n=4-6/group) were injected with SU5416 (Calbiochem; 20 mg/kg, subcutaneously) or vehicle (carboxymethylcellulose) and the mice were euthanized at the indicated time.

Morphometric analysis was performed on coded slides as described, using a macro developed by R.M.T. for Metamorph (Tuder, R. M., Zhen, L., Cho, C. Y., Taraseviciene-Stewart, L., Kasahara, Y., Salvemini, D., Voelkel, N. F., and Flores, S. C. 2003. Oxidative stress and apoptosis interact and cause emphysema due to vascular endothelial growth factor receptor blockade. *Am J Respir Cell Mol Biol* 29:88-97; Aherne, W. A., and Dunnill, M. S. 1982. *Morphometry*. London: E. Arnold. xiv, 205 pp).

Human lung tissue: Human lung tissue consisted of sections from fixed, paraffin embedded explanted lung tissue from COPD patients and patients without lung disease (collected at the Johns Hopkins University). The specimen collection and storage were approved by the Institutional Research Board from the Johns Hopkins University.

Apoptosis was detected in lysates (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498) or inflated fixed lung sections enabling focus on alveoli, rather than large airways and vessels (Tuder, R. M., Zhen, L., Cho, C. Y., Taraseviciene-Stewart, L., Kasahara, Y., Salvemini, D., Voelkel, N. F., and Flores, S. C. 2003. Oxidative stress and apoptosis interact and cause emphysema due to vascular endothelial growth factor receptor blockade. *Am J Respir Cell Mol Biol* 29:88-97), via active caspase-3 IHC (Abcam and Cell Signaling) or in situ labeling of apoptotic DNA on murine lung, using rat serum as negative control. The immunostaining for both active casaspase-3 and TUNEL was followed by DAPI (Molecular Probes) nuclear counter-staining. Executioner caspase (caspase-3 and/or -7) activity was measured with ApoONE Homogeneous Caspase-3/7 assay kit (Promega, Madison, Wis.). Human recombinant caspase-3 (Calbiochem) was utilized as positive control.

Lipid extraction and ceramide species measurement by tandem mass spectroscopy. Cellular or lung tissue lipids were extracted and lipid content was assessed by measurements of total lipid phosphorus ($P_i$) (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). After lipid extraction, the following individual molecular species of ceramides were monitored: 14:0, 16:0, 18:0, 18:1, 20:0, 24:0, and 24:1-ceramides and utilizing $C_{17}$ ceramide as internal standard, ceramides were measured by combined liquid chromatography-tandem mass spectrometry (LC-MS/MS) (27).

IHC. Paraffin sections were blocked with 10% rabbit (or goat serum if secondary antibody from goat) and incubated with antibodies or control antibodies. Polyclonal rabbit antiserum included EMAP II (1:500 dilute), capsase-3 (Cell signaling) and anti-MMP-12 (1:100, Sigma). Bound antibody was detected according to the manufacturer's instructions or a biotin-conjugated goat anti-rat IgG secondary antibody (Dianova, 1:100) and Streptavidin-coupled phycoerythrin (Dianova, 1:1000). For some application (anti-CD144, Pharmingen) cryosections were used. Sections were counterstained with DAPI and mounted with Mowiol 488 (Calbiochem). Microscopy was performed on either a Nicon Eclipse (TE200S) inverted fluorescent or a combined confocal/multiphoton (Spectraphysics laser, BioRad MRC1024MP) inverted system. Images and quantitative intensity (expression) data were processed by MetaMorph Imaging software (Universal).

Western blotting. Lung tissue was homogenized in RIPA buffer with protease inhibitors on ice and proteins were isolated by centrifugation at 10,000 g for 10 minutes at 4° C. BAL supernatants from transgenic mice or patients were collected and proteins were concentrated and precipitated by addition of trichloroacetic acid. Proteins were loaded in equal amounts (10 mg, unless otherwise noted) as determined by BCA protein concentration assay (Pierce, Rockville, Ill.). Total proteins were separated by SDS-PAGE using Novex gels (Invitrogen, Carlsbad, Calif.), followed by immunoblotting for EMAP II as previously described (Knies, U. E., Behrensdorf, H. A., Mitchell, C. A., Deutsch, U., Risau, W., Drexler, R C., and Clauss, M. 1998. Regulation of endothelial monocyte-activating polypeptide II release by apoptosis. *Proc Nati Acad Sci USA* 95:12322-12327). Briefly, samples were mixed with Laemmli buffer, boiled at 95° C. for 10 min and loaded onto 15% SDS/PAGE gels. Proteins were separated by electrophoresis and blotted onto nitrocellulose (Pierce) using a semidry blotting apparatus. Unspecific binding was reduced by blocking the membrane in TBS/0.1% Tween 20/5% nonfat dry milk. The primary antibody (rabbit anti-EMAP II antiserum SA 2847, diluted 1:1000 in TBS/0.1% Tween 20/5% BSA) was applied overnight at 4° C. After washing, the membranes were incubated in a peroxidase-coupled goat anti-rabbit IgG (Dianova/Jackson Immuno Research; diluted 1:3500 in blocking buffer) for 1 h at room temperature and developed using an enhanced chemilluminescence kit (Amersham Pharmacia Biotech). Immunoblotting for EMAP II in lung lysates or BAL was performed by incubation with EMAP II-specific antibody (rabbit serum, produced as described above) in a 1:250 dilution in TBST for 1 h at room temperature. The chemilluminescent signals were quantified by densitometry (ImageQuant; Amersham, Piscataway, N.J.) and normalized by housekeeping proteins (actin, GAPDH, or vinculin).

Statistical analysis was performed with SigmaStat software using ANOVA with Student-Newman-Keuls post hoc test. Statistical difference was accepted at $p<0.05$.

EXAMPLE 2

Effect of Cigarette Smoke Exposure or VEGF Receptor Inhibition on EMAP II Expression in the Mouse Lung To test the hypothesis that smoking induces cellular stress causing release of EMAP II, the effect of smoking on EMAP II protein production was measured. The extent of apoptosis induced by cigarette smoking in the mouse lung was also assessed. To more specifically address the correlation between endothelial cell death and EMAP II overproduction, the lung EMAP II expression in mice treated with a VEGF receptor blocker, which induces endothelial cell apoptosis was tested.

Mice susceptible to cigarette smoke-induced emphysema were exposed to cigarette smoke for various periods of time, from 4 days to 6 months. EMAP II expression was measured in lung lysates by western blotting and apoptosis by caspase-3 activity and ceramide production. Finally, lungs from mice treated with VEGF receptor blocker SU5416 (20 mg/kg subcutaneously) were tested for EMAP II expression by western plotting at 3 weeks, a time when lungs typically show morphometric changes of emphysema.

Cigarette smoke exposure for 4 days increased caspase-3 activity in lungs, and thus increased apoptotic activity as early as 1 week after cigarette smoke exposure in C57/BI6 mice (FIG. 2A), long preceding the increases in airspaces typical of emphysema that occurred at 6 months of cigarette smoke exposure (FIG. 2C). At 1 month the lung content of ceramide increased in DBA 2 mice (FIG. 2B). These early increases in apoptotic activity were paralleled by an increase in both the pro- and mature forms of EMAP II expression (FIGS. 3A and 3B). Similarly, in another experimental model of apoptosis-dependent emphysema, SU5416 induced a robust EMAP II expression at 4 weeks in the C57/BI6 mouse lung (FIG. 3C).

These results suggest an increase in apoptotic rates and EMAP II production in the emphysematous lungs of mice, including those exposed to cigarette smoke. While not wishing to be bound by theory, the increase in EMAP II may result from direct cell stress, or from apoptosis-activated caspases. Furthermore, EMAP II release may itself be responsible for inducing further lung endothelial cell apoptosis.

EXAMPLE 3

Effect of Elevated Lung EMAP II Levels on the Severity of Cigarette Smoke-Induced Injury in the Mouse Lung To test whether increases in EMAP II have an additive or a synergistic effect with cigarette smoking in the lung, EMAP II expression in the lungs was induced for 8 weeks prior to cigarette smoke exposure. The conditional transgenic over-expression system is presented in more detail in example 4.

An increase in baseline EMAP II levels in the lung followed by a 4 week cigarette smoke exposure profoundly elevated the levels of mature EMAP II and increased the number of inflammatory cells in the inter-alveolar/interstitial tissue consistent with a further increase in parenchymal inflammation compared to smoking alone.

These results suggest that EMAP II contributes to cigarette smoke-induced lung injury and may independently worsen or predispose the lung to a more severe inflammatory response to smoke.

EXAMPLE 4

Transgenic Induction of EMAP II in the Lung Causes Emphysema-Like Disease in Mice To study the mechanism by which increased lung levels of EMAP II trigger emphysema, a transgenic murine model of inducible expression of EMAP II in the lung was established using the tetracycline inducible transactivator (TTA) controlled by the lung epithelium-specific CCSP promoter. Although both EMAP II forms were available as inducible constructs, the mature EMAP II was initially assessed since it has been classically involved in the apoptosis and inflammatory effects of EMAP II. Furthermore, the pro-EMAP II is usually easily cleaved to generate mature EMAP II, making it difficult to assess its specific, mature-form-independent effects.

The transgenic mouse tet EMAP II (responder mouse) contained the mature form of EMAP II under a minimal promoter containing tetracycline-inducible sequences. This mouse line does not express elevated levels of EMAP II because it lacks the transactivator gene product. The responder mouse was crossed with homozygous transgenic mice containing the transactivator controlled by the lung epithelium specific CCSP promoter (CCSP mouse line), which in this form targets gene expression predominately in alveolar type II cells versus in Clara cells. Clark, J. C., et al. *Am J Physiol Lung Cell Mol Physiol* 280, L705-715 (2001); Li, Y., et al. *Cancer Res* 67, 8494-8503 (2007). The first generation of mice heterozygous for the EMAP II responder transgene and the CCSP transactivator with CCSP transactivator-only transgenic mice were compared. Of note, this CCSP transactivator-only transgene cannot induce EMAP II overexpression. With this design, CCSP transactivator background effects as described recently (Sisson, T. H., et al. *Am J Respir Cell Mol Biol* 34, 552-560 (2006)) and tetracycline effects can be ruled out, as both groups were treated with tetracycline. Furthermore, the tetracycline concentration used in this induction system is insufficient to ameliorate any inflammation and MMP activities. Expression was analyzed by Western of BAL and lung lysates and by IHC of lung sections using EMAP II antiserum. To determine whether long term EMAP II over-expression in the lung induces an emphysema-like phenotype, double transgenic mice with tetracycline in the drinking water were treated for up to 6 months.

Figures 4A, 4B:
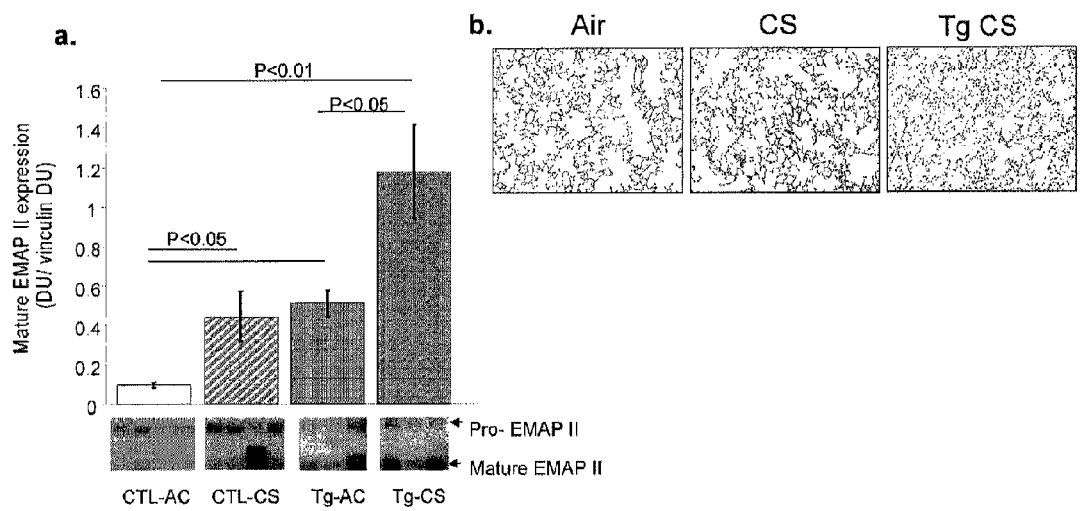
FIG. 4A shows the effect of cigarette smoke exposure on EMAP II levels in lung lysates.
FIG. 4B shows the effect of cigarette smoke exposure on the amount of inflammatory cells in lung tissue.
Figures 5B, 5D:
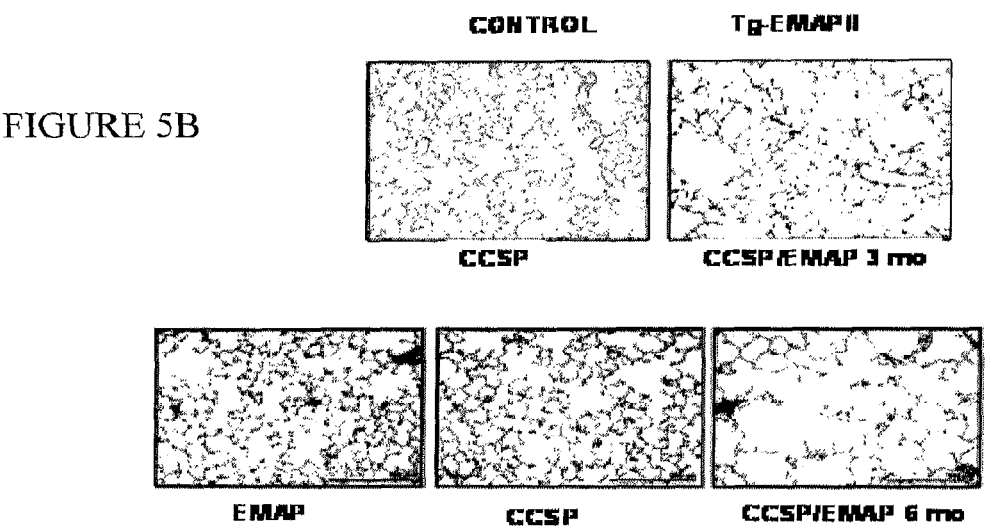
FIG. 5B is a lung section showing the alveolar after tetracycline treatment.
FIG. 5D is a lung section showing the alveolar after tetracycline treatment.
Figure 5A:
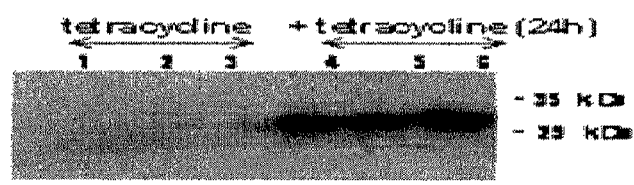
FIG. 5A is a western blot showing the induction of EMAP II in mice after 24 hours of tetracycline treatment.
Figure 5C:
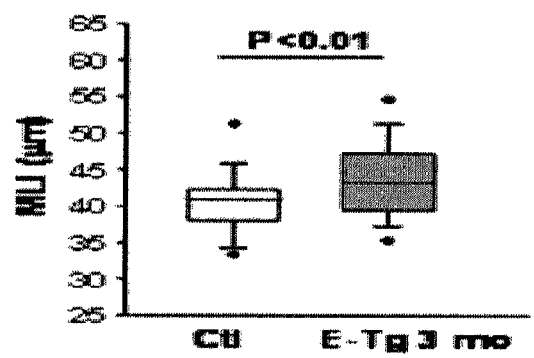
FIG. 5C is a bar graph showing the mean linear intercept of lung tissue of mice treated with tetracycline and controls.
Figure 5E:
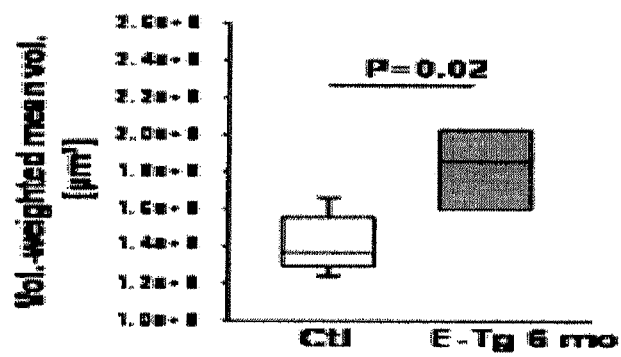
FIG. 5E is a bar graph showing the volume weighted mean volume of lung tissue of mice treated with tetracycline and controls.
Figure 7A:
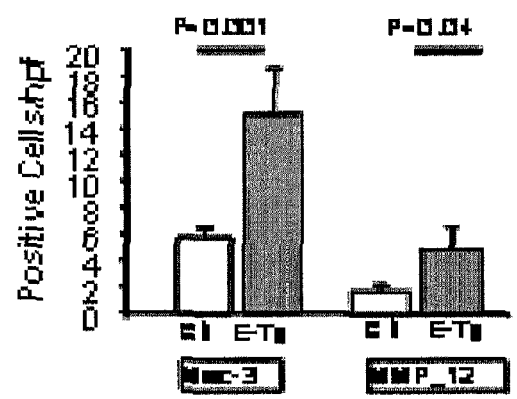
FIG. 7A is a bar graph showing the number of cells in the lungs of mice overexpressing EMAP II compared to a control.

Transgenic induction of EMAP II caused high EMAP II secretion into the lungs of double transgenic mice after as early as 24 h (FIGS. 3B, 4B and 5A). Of note, the EMAP II expression pattern in the lung parenchyma resembled typical staining pattern for alveolar type II cells, which is in line with the reported selectivity for this transgenic promoter. EMAP II double transgenic mice treated for 3 or 6 months with tetracycline to induce EMAP II expression displayed significant emphysema-like increase in airspace (FIG. 7A). This was measured both by the mean linear intercept and the recently established method of volume-weighted mean airspace volume. Morphological parameters for emphysema appear to increase proportional to the duration of EMAP II induction, which is reflected by morphometry: the volume-weighted mean airspace volume was 1.36E+08±0.15, n=5 in control mice; 1.56E+08±0.3 in EMAP II transgenic mice induced for 3 months; and 1.91E+08±0.3, n=6, in those induced for 6 months; p=0.027)

Increased EMAP II production in the lungs leads to formation of emphysema-like morphological changes. This is the first evidence that excessive levels of a protein causing endothelial cell death leads to emphysema.

EXAMPLE 5

Excessive EMAP II Production in the Lung Causes Pulmonary Cell Apoptosis

To address the hypothesis that EMAP II over-production promotes emphysema via endothelial cell apoptosis, apoptosis in the lungs of EMAP II-overexpressing mice was assessed. To determine the EMAP II-specificity of apoptosis, and to test in vivo the efficacy of an EMAP II-neutralizing antibody, the anti-EMAP antibody was administered to a group of EMAP II transgenic animals.

Fluorescent microscopy with specific active caspase-3 antibody of lung sections from EMAP II/CCSP double transgenic (EMAP II tg) or CCSP control transgenic animals (ctl) was used to detect the presence and localization of apoptosis in the lung. Anti-VE-cadherin antibody was used to test for colocalization of apoptosis with endothelial cells. In addition, lung lysates were tested for caspase-3 activity by fluorimetric enzymatic assay (Promega). For the neutralization experiment, EMAP II tg (induced for 48 h before harvesting the lungs) received anti-EMAP II rat monoclonal antibody or isotype IgG control, by a single injection i.p., 12 h after the induction.

Figure 6A:
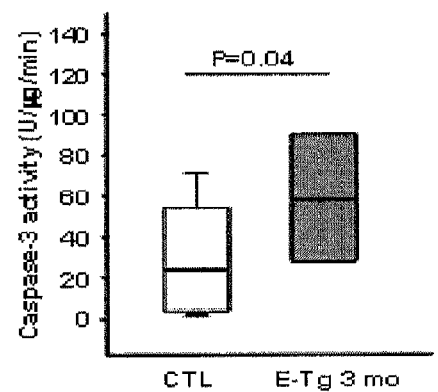
FIG. 6A is a graph showing the caspase-3 activity in lung lysates of single or EMAP II double transgenic mice.
Figure 6B:
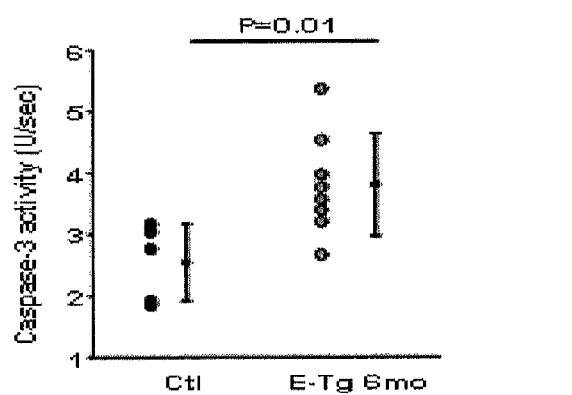
FIG. 6B is a graph showing caspase-3 activity in lung lysates of single or EMAP II double transgenic mice.
Figure 6C:
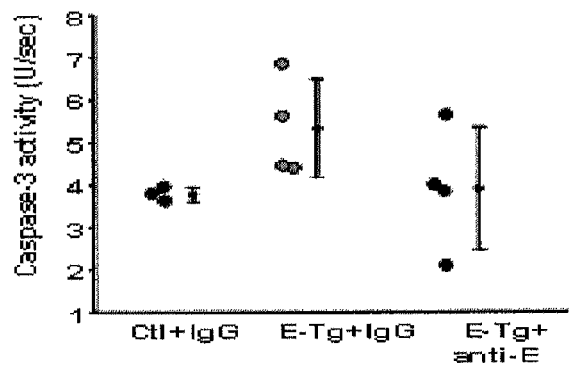
FIG. 6C is a graph showing caspase-3 activity in lungs of single or EMAP II double transgenic mice treated with non-specific control IgG and neutralizing EMAP II antibody.

EMAP II significantly increased the number of caspase-3 positive cells in the lung parenchyma of EMAP II tg versus ctl (~6 fold, p=0.003, by fluorescence quantitation using Metamorph on blinded slides) as early as 3 weeks after induction. The increased lung apoptosis persisted after 3 mo and 6 mo of EMAP II inductions as assessed by both IHC and caspase-3 activity from lung lysates (FIGS. 6A and 6B). The majority of caspase-3 positive cells were endothelial cells. There was a trend for decreased apoptosis in mice receiving neutralizing EMAP II antibody (FIG. 6C).

It is thought that changes by in situ detection of activated caspase-3 were more dramatically significant due to the higher signal to noise ratio in lysates resulting from having many other non-dying cells other than endothelial cells. Finally, although not yet statistically significant, the neutralizing effects of anti-EMAP II antibody are extremely encouraging in that apoptosis observed is EMAP II dependent and that the neutralizing antibody is effective in vivo. Taken together these data support the conclusion that endothelial cell apoptosis may be a key event in EMAP II-induced emphysema formation.

EXAMPLE 6

Effect of Lung-Specific EMAP II Overexpression on the Monocyte Recruitment in the Lung It was previously shown that EMAP II attracted and activated monocytes in a dose-dependent manner, caused inflammation when locally injected, and triggered leukostasis in the lung upon systemic application. Kao, J., et al., *J Biol Chem* 269, 25106-25119 (1994); Kao, J., et al., *J Biol Chem* 269, 9774-9782 (1994). The chemotactic effect of EMAP II on monocytes may be important in the inflammatory responses associated with emphysema.

Confocal imaging of fluorescent immunostaining of markers for lung macrophage accumulation and activation in lung sections from EMAP II/CCSP double transgenic vs. CCSP single transgenic animals was performed using MAC-3- (macrophage marker) as well as TNFα-, MMP-9-, and MMP-12-specific antibodies.

Figure 7B:
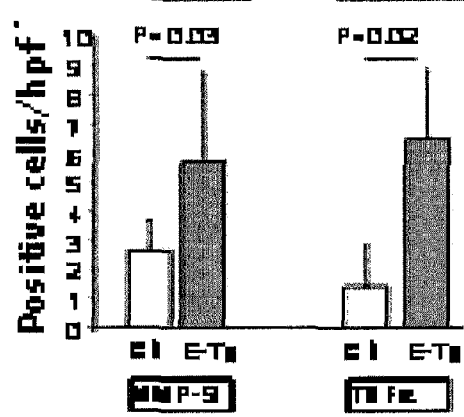
FIG. 7B is a bar graph showing the quantification MMP-9- and TNFα-positive cells.

The lung specific overexpression of mature EMAP II dramatically increased the numbers of MAC-3-expressing cells along with staining for TNFα-, MMP-9, MMP-12 in the lung (FIGS. 7A-7B). The vast majority of TNFα-, MMP-9, MMP-12 and MAC-3 positive cells displayed a large nuclear phenotype, characteristic for macrophages, whereas MMP-12-positivity colocalized not only with Mac-3 (FIG. 7A), but also with other cells within the alveolar wall, possibly epithelial cells.

The increase in Mac-3 positive cells was most likely due to recruitment of monocytes form the circulation to the lung, as the proliferation capacity of already resident lung macrophages is extremely low. These macrophages may be a source of inflammatory activation in the lungs of EMAP II transgenic.

EXAMPLE 7

Both Pro- and Mature EMAP II-Induce Significant Apoptosis in Human Primary Microvascular Lung Endothelial Cells Situations associated with stress can induce both forms of EMAP II. It is not known which form is more potent in inducing endothelial cell apoptosis and whether the mechanism by which this occurs is form-dependent. These detailed mechanistic assays can only be done in cell cultures. However to increase their significance, only primary lung microvascular endothelial cells of human origin, commercially obtained (Lonza) were tested.

Primary human lung microvascular endothelial cells were treated with recombinant pro- or mature-EMAP II at 10-16 μg/ml. Apoptosis was measured by caspase-3 activity and Annexin/PI staining by flow cytometry.

Figure 8A:
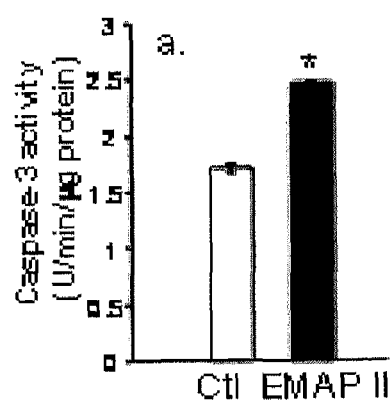
FIG. 8A is a bar graph showing the effect of EMAP II overexpression on caspase-3 activity.
Figure 8B:
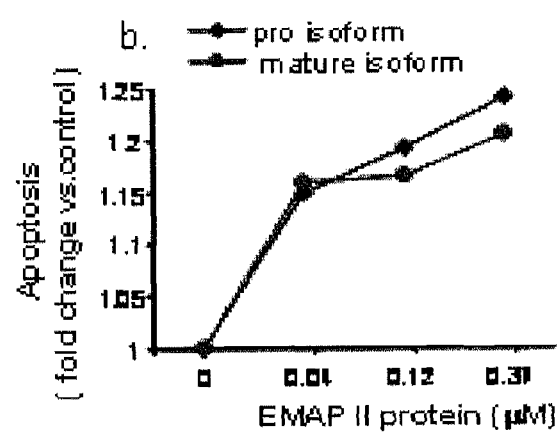
FIG. 8B is a graph showing the effect of treatment of lung microvascular endothleial cells with recombinant proteins comprising the pro- and mature isoforms of EMAP II on apoptosis.
Figure 8C:
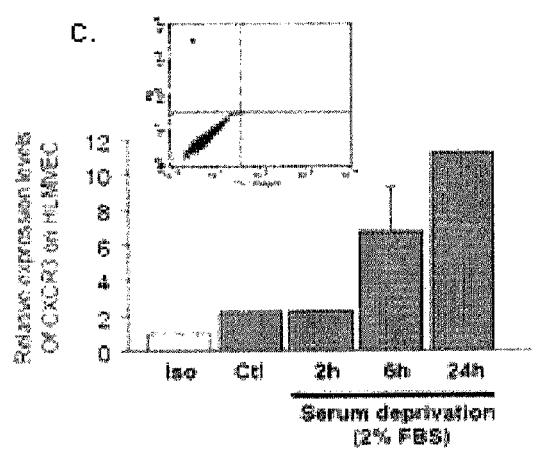
FIG. 8C is a bar graph showing the expression levels of CXCR3 in cells cultured with low serum.
Figure 8D:
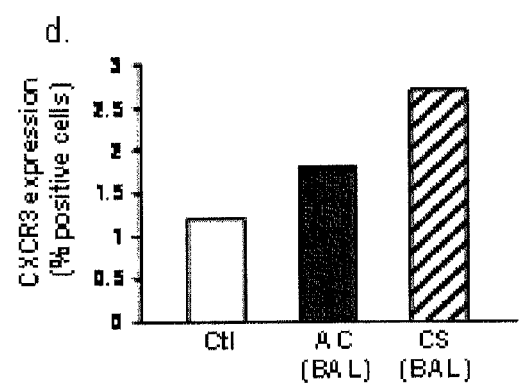
FIG. 8D is a bar graph showing the expression levels of CXCR3 in cells treated with acellular BAL from mice exposed to cigarette smoke or air.
Figure 8E:
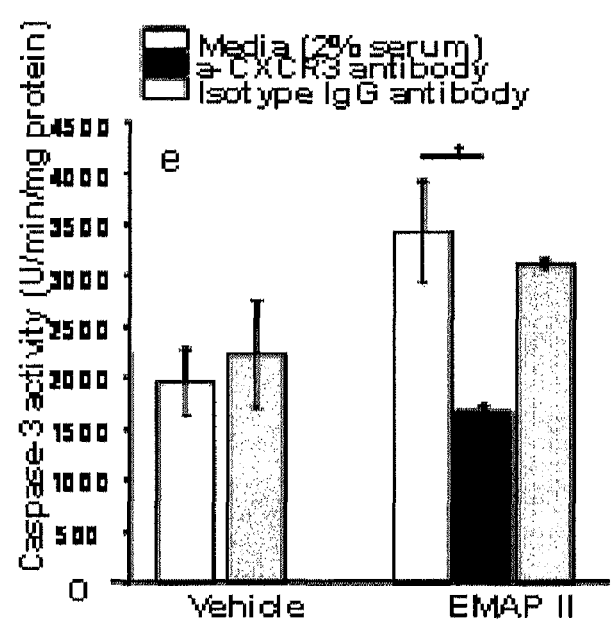
FIG. 8E is a bar graph showing the effect of anti-CXCR3 antibody on caspase-3 activity.

Treatment with both forms of EMAP II resulted in increased apoptosis as measured by caspase-3 activity and Annexin/PI staining (FIGS. 8A and 8E, respectively).

Both the pro- and mature EMAP II forms appeared equally potent at inducing endothelial cell apoptosis in culture conditions.

EXAMPLE 8

The Stress-Sensitive CXCR3 Receptor Mediates EMAP II-Induced Lung Endothelial Cell Apoptosis To investigate whether the CXCR3 receptor mediates EMAP II-induced lung endothelial cell apoptosis, its expression on primary human lung microvascular endothelial cells was initially assessed and secondly, its function was inhibited by specific blocking antibodies.

Primary human lung microvascular endothelial cells were cultured in normal growth media, as well as in media containing low serum concentration (2%), or even treated with acellular BAL from smoked or control mice. The BAL was concentrated (50-fold) and cells were incubated with a volume representing 10% of the original undiluted cellular BAL. CXCR3 was detected by using labeled anti-CXCR3 antibody detected by FACS. To assess the role of the CXCR3 caspase-3 activation in lung microvascular endothelial cells, cells with blocking anti-CXCR3 antibodies were pretreated (1 µg/ml, pretreated for 30 min).

Primary human lung microvascular endothelial cells express CXCR3 at low levels. Stressful conditions such as serum starvation, treatment with BAL from smoked but not from non-smoked mice, or even electroporation (FIG. 9) increased significantly its expression (FIG. 8A-8D). Anti-CXCR3 antibodies, but not isotype IgG antibodies significantly reduced mature EMAP II-induced endothelial cell death (FIG. 8A-8D).

These results are strong evidence that EMAP II-induced endothelial cell apoptosis in the lung may be mediated primarily by the CXCR3 receptor. This implies that CXCR3 mediates the functional effects of EMAP II on both endothelial cells and monocytes and may be important for the development of cigarette smoke emphysema.

EXAMPLE 9

Figure 10:
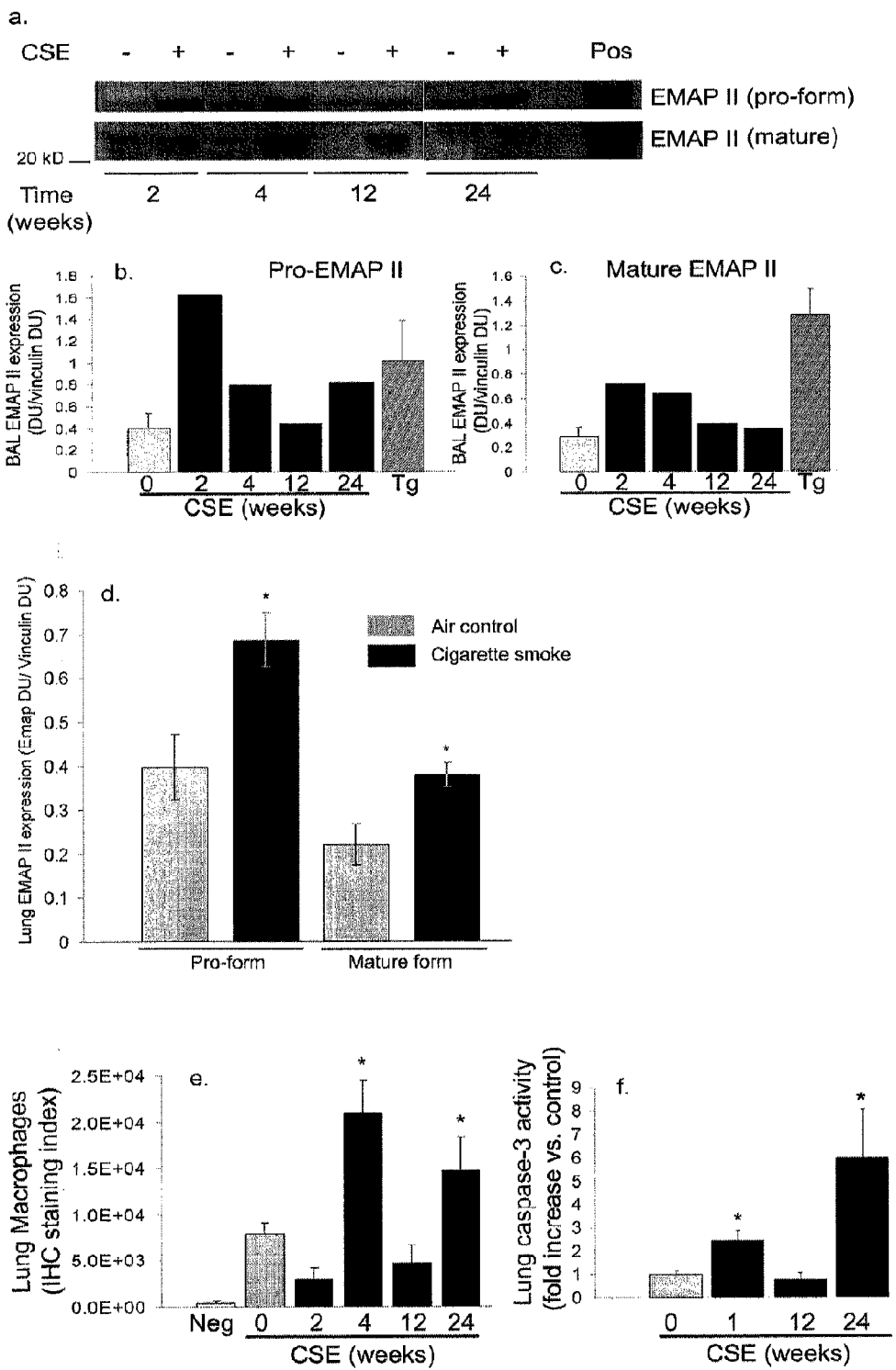
FIG. 10A is an immunoblot showing the effect of cigarette smoke exposure on EMAP II expression in the mouse lung.
FIG. 10B is a bar graph showing the effect of cigarette smoke exposure on expression of pro-EMAP II in mouse lung.
FIG. 10C is a bar graph showing the effect of cigarette smoke exposure on expression of mature EMAP II in mouse lung.
FIG. 10D is a bar graph showing EMAP II expression in the lung parenchyma of DBA2 mice exposed to cigarette smoke for 4 weeks.
FIG. 10E is a bar graph showing lung macrophage accumulation in pulmonary parenchyma in response to cigarette smoke exposure.
FIG. 10F is a bar graph showing lung apoptosis as measured by capsase-3 activity assay in lung lysates following cigarette smoke exposure.
FIG. 10G is an immunoblot showing lung EMAP II expression in a mouse model of apoptosis-dependent emphysema.
Figure 10G:
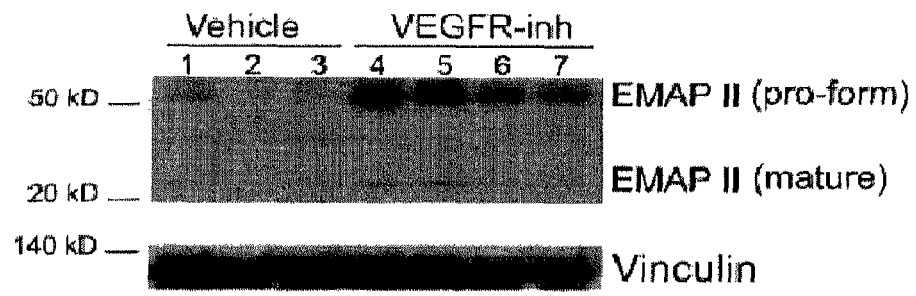

Cigarette Smoke Increased the Expression of Both EMAP II Forms in the Mouse Lung Based on previous findings that mature EMAP II is released by apoptosis and the proform upon stress, the induction of EMAP II in the lung in vivo upon exposure to cigarette smoke was investigated. Therefore, EMAP II expression was measured in two inbred mouse strains, C57/Bl6 and DBA2, which reportedly develop emphysema after chronic exposure to cigarette smoke for 6 or 4 months, respectively. Cigarette smoke exposure (for up to 24 weeks) profoundly increased both the pro- and mature forms of EMAP II (approximately 8- and 2-fold respectively) secreted in the bronchoalveolar lavage (BAL) and detected by western blotting (FIG. 10A). Equal volume (100 µl) of acellular BAL from each mouse was pooled (n=5 per time point), then equally concentrated (10×) and equally loaded (10 µl) in each lane. Specific EMAP II antibody (1:250) detected both the pro- and the mature forms of the EMAP II in the lavage. BAL from the EMAP II over-expressing transgenic (Tg) mice was utilized as positive (Pos) control. Similar increases in the two forms of EMAP II expression were noted in the lung parenchyma of DBA2 mice exposed to cigarette smoke for 4 weeks (FIG. 10B). Interestingly, in a distinct experimental model of apoptosis-dependent murine emphysema which develops secondary to VEGF receptor inhibition, EMAP II expression was also markedly upregulated in the lungs of mice which developed airspace enlargement compared to control mice, but predominantly in the pro-form (FIG. 10G). FIG. 10G shows EMAP II expression in the lung parenchyma of C57/Bl6 mice at four weeks after treatment with the VEGF receptor inhibitor (VEGFR-inh). Each lane was loaded with 40 µg lung lysate from individual mice treated with vehicle (carboxymethyl cellulose) or the VEGFR-inh SU5416 (20 mg/kg, subcutaneous). Vinculin was immunoblotted as loading control. The kinetics of EMAP II elevation in response to cigarette smoking demonstrated that the increase in lung EMAP II secretion preceded that of alveolar macrophage accumulation, first noted at 4 weeks, but not 2 weeks of cigarette smoke exposure (FIG. 10E). The kinetic relationship of the EMAP II increase with the caspase-3 activation in the lung was more complex, as significant caspase-3 activation was noted throughout the time course of the EMAP II increases in response to cigarette smoking in mice (FIG. 10F). Since EMAP II's biological properties include monocyte chemoattraction and apoptosis of proliferative and hypoxic endothelial cells, EMAP II could play an important role in the inflammatory and apoptotic responses in the lung in response to cigarette smoke exposure.

EXAMPLE 10

EMAP II Induced Apoptosis in Primary Human Lung Microvascular Endothelial Cells Via the Chemokine Receptor CXCR3

Previously, mature EMAP II was suggested to exert anti-angiogenic activities by inducing apoptosis in growing endothelial cells within tumor vessels and in vitro. Since the occurrence of excessive apoptosis of alveolar endothelial cells has been implicated in the development of emphysema, it was investigated whether differentiated primary human lung microvascular endothelial cells are susceptible to the apoptotic effects of EMAP II. Both the pro- and the mature EMAP II forms triggered comparable dose-dependent apoptosis in lung endothelial cells at 4 h, which was sustained for up to 18 h (FIGS. 11A and 11B). Apoptosis was measured by Annexin V and propidium iodide staining detected by flow cytometry and expressed as fold increase in cells treated with the indicated concentrations of pro- and mature EMAP II forms for 4 h compared to untreated cells. Results are expressed as mean (+SEM; *p<0.05 vs. control, n=2). The timecourse of apoptosis (FIG. 11B) induced by mature EMAP II treatment (10 µg/ml) was measured by Annexin V/propidium iodide staining (results expressed as mean+SEM; *p<0.05 vs. control, n=3). The endothelial cell apoptosis triggered by EMAP II (mature form, 10 µg/ml) was associated with increased caspase-3 activity (FIG. 11D) and decreased cellular proliferation (by 31% at 16 h compared to control untreated cells), as measured by Ki staining (data not shown).

Figure 11E:
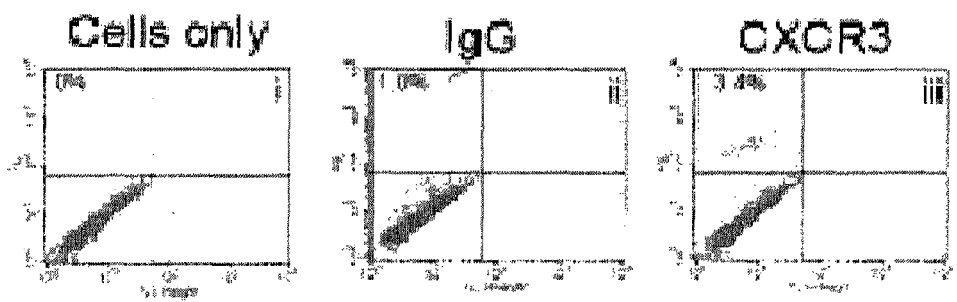
FIG. 11E shows CXCR3 expression in primary human lung microvascular endothelial cells.
Figure 11:
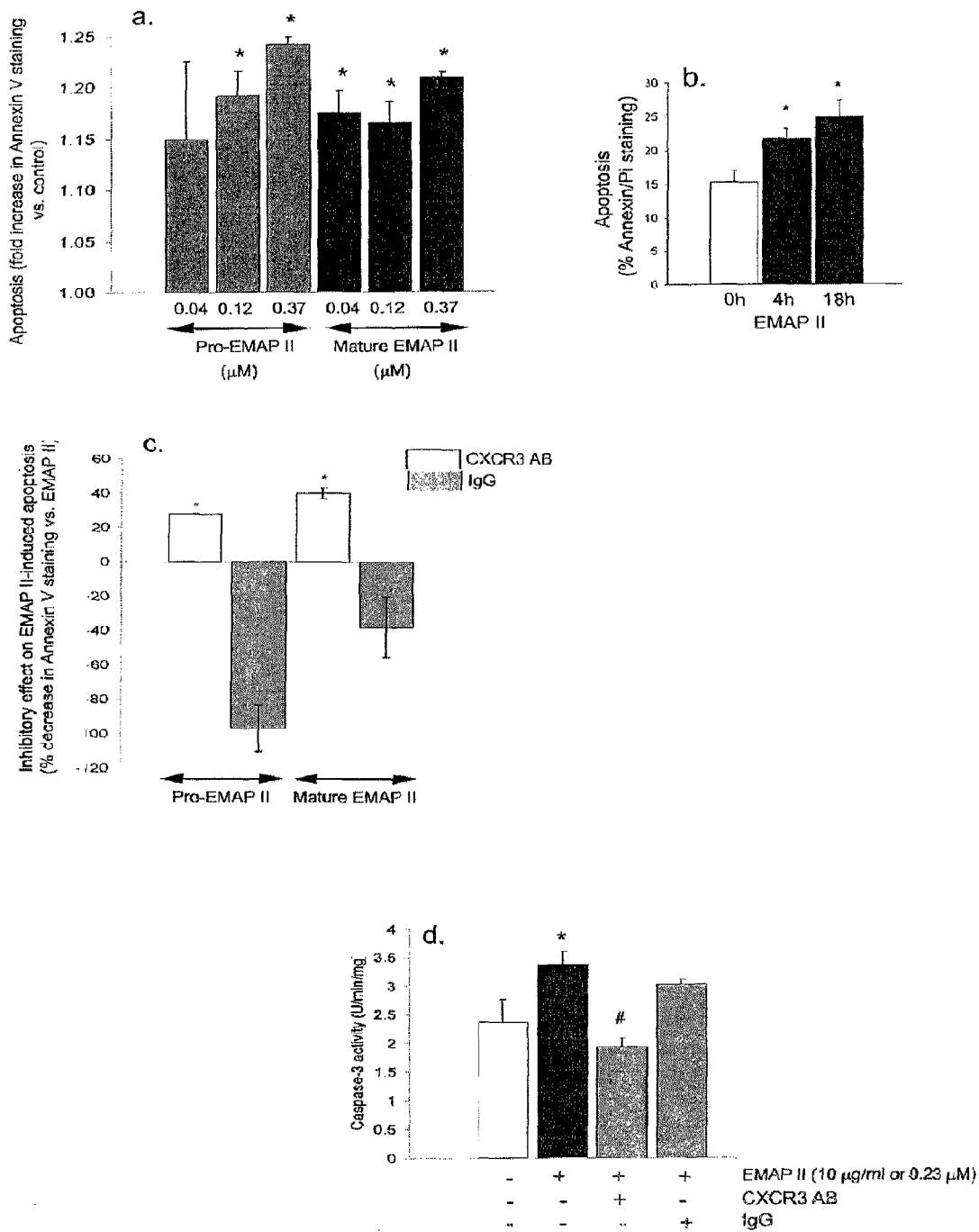
FIG. 11A is a bar graph showing pro-apoptotic effects of EMAP II in human lung endothelial cells treated with different concentrations of pro- and mature EMAP II forms for 4 h compared to untreated cells.
FIG. 11B is a bar graph showing pro-apoptotic effects of EMAP II in human lung endothelial cells treated with mature EMAP II over time.
FIG. 11C is a bar graph showing the inhibitory effect of CXCR3-specific antibody on EMAP II (10 µg/ml) -induced endothelial cell apoptosis.
FIG. 11D is a bar graph showing the effect of CXCR3-specific antibody compared to control IgG on EMAP II-induced caspase-3 activity in human lung endothelial cells.

Recently, it has been shown that CXCR3 is the functional receptor for EMAP II in endothelial progenitor cells and circulating blood monocytes. To investigate whether the CXCR3 receptor mediates EMAP II-induced apoptosis in lung endothelial cells, its expression on primary human lung microvascular endothelial cells was assessed. These endothelial cells expressed detectable levels of CXCR3 in standard culture conditions (10% fetal bovine serum), measured by immunostaining with a CXCR3-specific antibody (10 µg/ml), using an isotype-specific IgG as control (FIG. 11E). Next, utilizing specific blocking antibodies, it was determined whether the CXCR3 receptor was functionally involved in EMAP II-induced apoptosis of lung endothelial cells. Specific CXCR3 antibody, but not isotype IgG antibodies significantly reduced both the pro- and mature EMAP II-induced endothelial cell death (FIGS. 11C and 11D), thus implicating the chemokine CXCR3 receptor in both EMAP II-induced monocyte migration and lung endothelial cell apoptosis.

EXAMPLE 11

Figure 12:
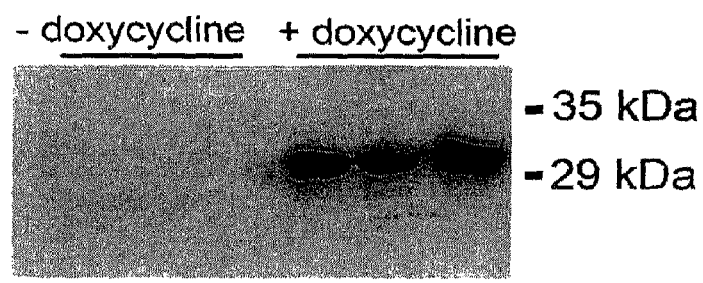
FIG. 12 is an immunoblot showing EMAP II expression detected in bronchoalveolar lavage in the absence of or after 24 h of doxycycline treatment in double transgenic EMAP II/CCSP-rtTA mice.

EMAP II Overexpression in the Lungs of Transgenic Mice Triggered Endothelial Apoptosis To functionally link the induction of endothelial cell death and alveolar macrophage migration by EMAP II to the smoke-induced upregulation of EMAP II in the lungs a transgenic murine model of inducible expression of EMAP II in the lung was established using a tetracycline inducible transactivator (TTA) controlled by the lung epithelium-specific CCSP promoter. After transgenic overexpression induced by the addition of tetracycline in the drinking water, the mature EMAP II expression was analyzed by IHC of lung sections using EMAP II-specific antiserum and by Western blotting of BAL and lung lysates. Transgenic induction of mature EMAP II in the lung parenchyma resembled a distribution typical of that of alveolar type II cells. Induction with tetracycline markedly increased EMAP II secretion into the lungs, detected in the bronchoalveolar lavage of double transgenic mice as early as 24 h (FIG. 12). To determine whether long-term EMAP II over-expression in the lung induces endothelial apoptosis and macrophage accumulation, we treated double transgenic mice (overexpressing EMAP II) and single transgenic (CCSP-only as control) mice with tetracycline in the drinking water for up to 6 months.

Figure 13:
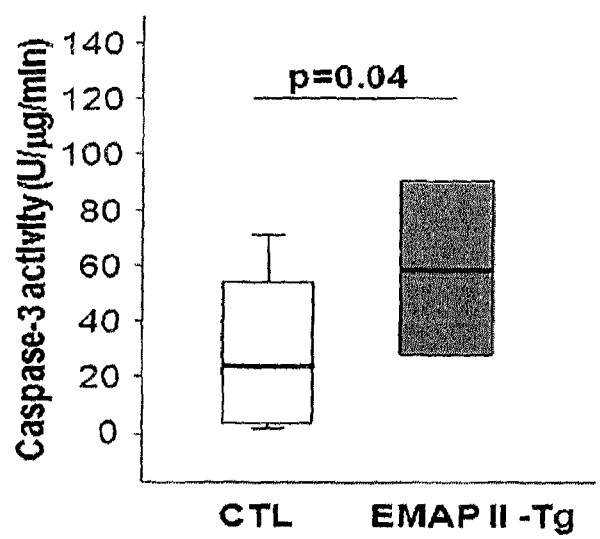
FIG. 13 is a box-plot of caspase-3 activity in lung lysates of single transgenic control (Ctl) or EMAP II double transgenic (E-Tg) animals after 3 week induction with doxycycline.

Apoptosis in the lungs of transgenic mice was assessed by caspase-3 activity in lung lysates and by confocal imaging of fluorescent immunostaining for active caspase-3 and caspase-3 activity. In the lung parenchyma of doxycycline-induced EMAP II expressing transgenic animals more active caspase-3 positive cells were observed in EMAP II overexpressing animals compared to control mice expressing only the Tet-responsive construct at 3 weeks after EMAP II induction. This increase in active caspase-3 staining concurred with increased caspase-3 activity in lungs. When lung lysates of EMAP II overexpressing mice were compared to control mice there was a marked, almost three-fold increase (p=0.04) in caspase-3 activity (FIG. 13). The thick horizontal line represents the median, and whiskers show the $5^{th}$ and $95^{th}$ percentile. The increased lung apoptosis was sustained for 1.5 and 6 months after EMAP II induction as assessed by both caspase-3 IHC and activity in lung lysates (data not shown). Of note, the majority of caspase-3 positive cells were alveolar endothelial cells based on double staining with VE-cadherin using confocal microscopy.

EXAMPLE 12

Figure 14:
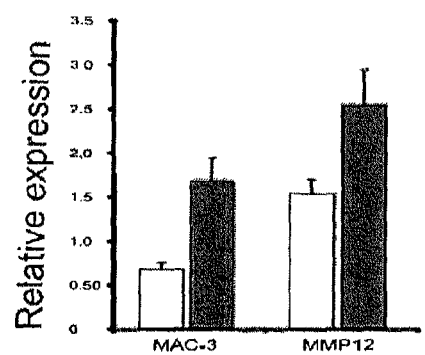
FIG. 14 is a bar graph showing relative expression of macrophage cell markers Mac-3 and MMP-12 in the lungs of control (white) and EMAP II overexpressing (gray) mouse lung parenchyma.

Lung-Specific EMAP II Overexpression Increased Alveolar Macrophage Accumulation and MMP-12 Expression Compared to control mice (FIG. 14), EMAP II overexpressing mice manifested a robust increase in the lung immunostaining for the macrophage cell-type marker Mac-3 after 6 months of transgene induction. The relative expression represents the ratio of immunostaining fluorescence intensity to the number of DAPI-stained nuclei in the respective field. This increase was associated with augmented expression of macrophage metalloelastase, MMP-12, which colocalized predominantly with the macrophages marker Mac-3 in double immunofluorescence microscopy.

EXAMPLE 13

Figure 15:
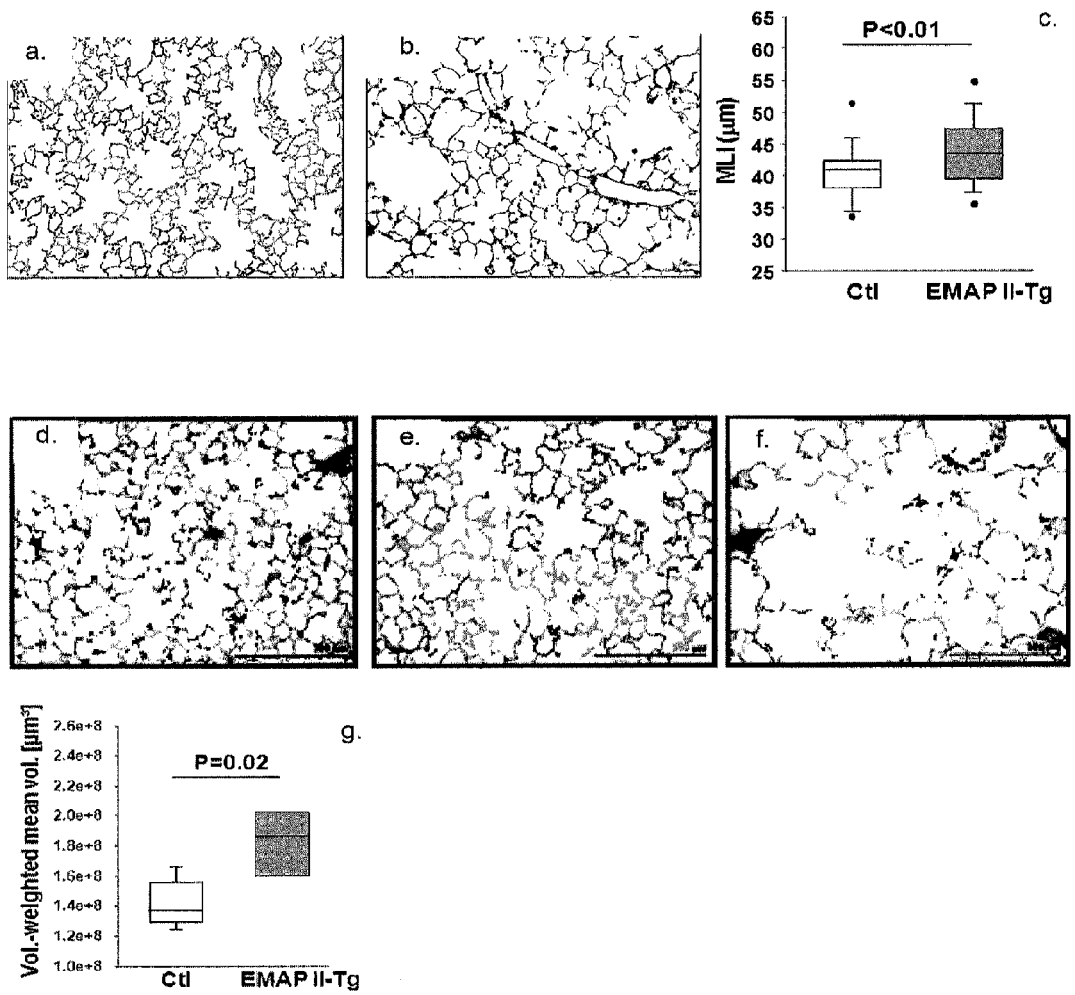
FIG. 15A is a photomicrograph showing increased airspace enlargement in EMAP II overexpressing mice after 3 months of doxycycline treatment of single transgenic CCSP-rtTA.
FIG. 15B is a photomicrograph showing increased airspace enlargement in EMAP II overexpressing mice after 3 months of doxycycline treatment of double transgenic EMAP II/CCSP-rtTA.
FIG. 15C is a box-plot showing increased airspace enlargement in EMAP II overexpressing mice after 3 months of doxycycline treatment.
FIG. 15D is a photomicrograph showing increased airspace enlargement in EMAP II overexpressing mice after 6 months of doxycycline treatment of single transgenic EMAP II.
FIG. 15E is a photomicrograph showing increased airspace enlargement in EMAP II overexpressing mice after 6 months of doxycycline treatment of single transgenic CCSP-rtTA.
FIG. 15F is a photomicrograph showing increased airspace enlargement in EMAP II overexpressing mice after 6 months of doxycycline treatment of double transgenic EMAP II/CCSP-rtTA.
FIG. 15G is a box-plot showing volume-weighted mean airspace volume after 6 months of doxycycline treatment of single transgenic EMAP II.

Lung-Specific EMAP II Overexpression Induced Emphysema-Like Pathology of the Lung Endothelial cell death, alveolar macrophage accumulation and MMP-12 expression are implicated in emphysema pathogenesis. Lung-specific EMAP II overexpression for up to 6 months significantly increased airspace diameters, consistent with simplification of alveolar structures (FIGS. 15A-15G). The airspace enlargement was progressive, noted on hematoxyllin-eosin stained lung sections and measured by the volume-weighted mean airspace volume, which significantly increased from 1.36E+08 (±0.15, n=5) in control mice to 1.56E+08 (±0.3 SD, n=6) at 3 months (not shown) and 1.91E+08 (±0.3, n=6) at 6 months of EMAP II lung overexpression (p=0.027) (FIG. 15G). The loss of alveolar septae was further supported by an increase in the mean linear intercept in the mice overexpressing EMAP II for 3 months compared to control mice (FIG. 15C). Note that the bar in FIGS. 15A, 15B, 15D, 15E and 15F represents 300 µm. These data suggest that EMAP II increase alone may be sufficient to trigger emphysema-like airspace enlargement.

EXAMPLE 14

Figure 16:
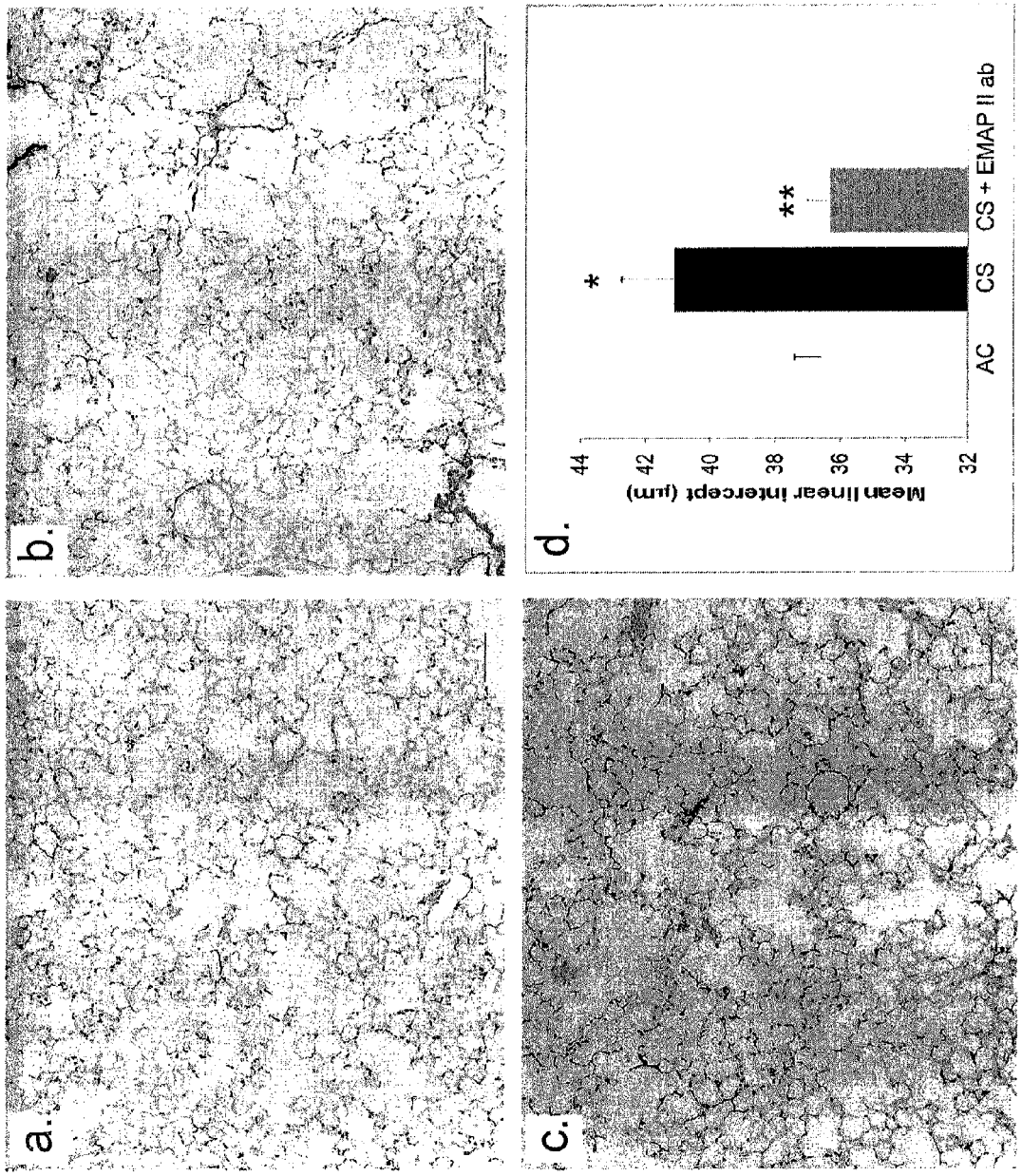
FIG. 16A is photomicrograph showing inhibitory effect of EMAP II neutralization on cigarette smoke-induced airspace enlargement in mice exposed to ambient air.
FIG. 16B is photomicrograph showing the inhibitory effect of EMAP II neutralization on cigarette smoke-induced airspace enlargement in mice exposed to cigarette smoke for 4 months.
FIG. 16C is photomicrograph showing the inhibitory effect of EMAP II neutralization on cigarette smoke-induced airspace enlargement in mice exposed to cigarette smoke for 4 months plus specific EMAP II antibody administered via inhalation during months 3 and 4.
FIG. 16D is a bar graph showing the inhibitory effect of EMAP II neutralization on cigarette smoke-induced airspace enlargement in mice exposed to ambient air control (AC), cigarette smoke (CS), or cigarette smoke plus specific EMAP II neutralizing antibodies (CS+EMAP II ab)

Specific Neutralization of Secreted EMAP II Inhibits Cigarette Smoke-Induced Airspace Enlargement in Mice To investigate whether an excess of secreted EMAP II is also necessary for the pathogenesis of airspace enlargement in response to cigarette smoking, EMAP II was neutralized by administration of specific monoclonal antibodies in mice exposed to cigarette smoking. The DBA2 mice, which develop significant airspace enlargement after 4 months of cigarette smoke exposure, were first exposed to cigarette smoke for 2 months. For the following 1 month of exposure, specific EMAP II antibodies or isotype IgG (1 mg/kg) were administered thrice weekly via nebulization. At the end of the 4 month of total cigarette smoke exposure, lung morphometry demonstrated significant increase in airspace size consistent with simplification of alveolar structure, reminiscent of emphysema, in response to smoking but not ambient air (FIGS. 16A-16C, bar is 100 µm). While inhaled IgG did not have an inhibitory effect on cigarette smoke-induced airspace size (not shown), treatment of mice with inhaled EMAP II antibody significantly inhibited the airspace enlargement induced by cigarette smoking (FIGS. 16C and 16D). These data suggest that application of neutralizing antibodies can reduce emphysema development even after a considerable time of smoke exposure.

EXAMPLE 15

Synergistic Effects of EMAP II and Cigarette Smoke Exposure in the Lung

Figure 17:
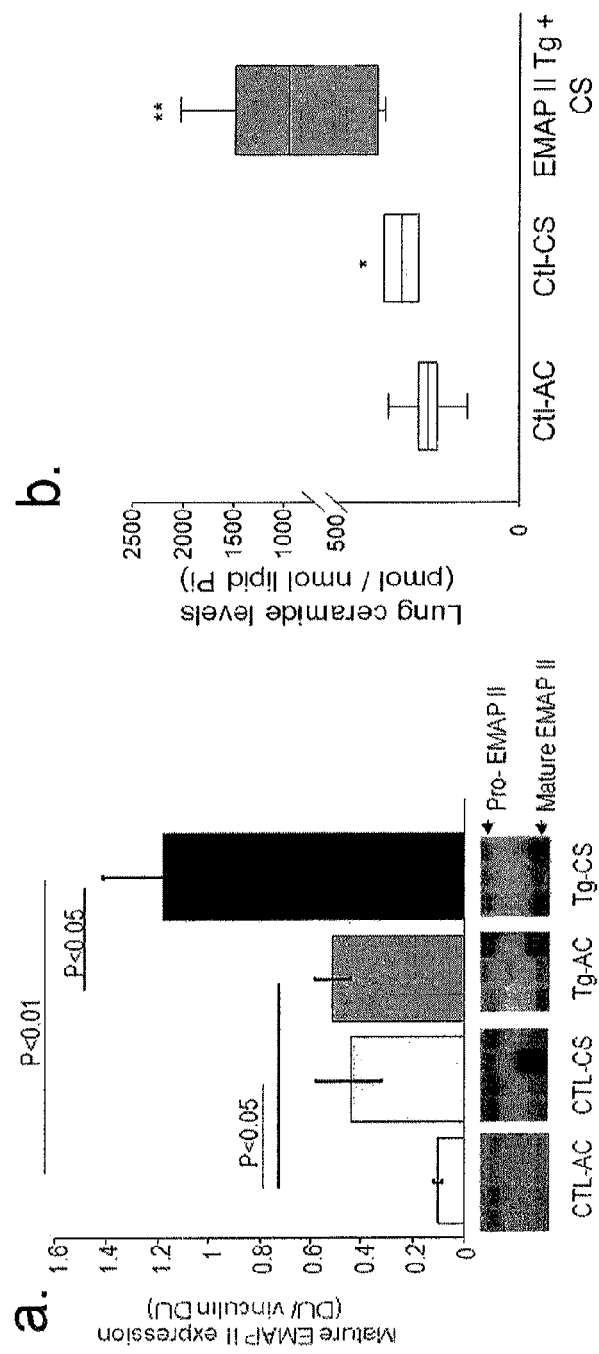
FIG. 17A is shows the synergistic effect of EMAP II and cigarette smoke on lung injury in mice by measuring EMAP II levels.
FIG. 17B is a box-plot showing ceramide levels normalized for lipid phosphorus (Pi) content of mice exposed to air and cigarette smoke.

Having shown that EMAP II is both sufficient and necessary in smoke induced emphysema, it was next asked whether enhanced levels of baseline EMAP II in the lung sensitize the lungs to cigarette smoke-induced injury, specifically apoptosis and macrophage inflammation. Increased lung levels of EMAP II were achieved in the double transgenic mice by tetracycline administration for 8 weeks. Double transgenic (EMAP II overexpressing) or single transgenic control mice were then exposed to cigarette smoking daily, five times a week, for 4 weeks. Lungs were then assessed for levels of apoptosis by extracting and measuring whole lung apoptosis-signaling ceramides, as reported previously (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). At this time point of cigarette smoke exposure, lungs of wild-type mice express only modest increases in ceramides (Petrache, I., Medler, T. R., Richter, A. T., Kamocki, K., Chukwueke, U., Zhen, L., Gu, Y., Adamowicz, J., Schweitzer, K. S., Hubbard, W. C., at al. 2008. Superoxide dismutase protects against apoptosis and alveolar enlargement induced by ceramide. *Am J Physiol Lung Cell Mol Physiol* 295:L44-53). Interestingly, there was a dramatic increase in ceramides in the lungs of mice overexpressing EMAP II prior to cigarette smoking compared to either EMAP II overexpression or cigarette smoking alone (FIG. 17A). Similarly the number of lung macrophages measured by IHC using F4/80 antibody increased synergistically in the mice overexpressing EMAP II prior to cigarette smoking (FIG. 17B) compared to mice exposed for the same duration to either stimulus alone. Levels of lung ceramide, a marker of alveolar apoptosis elevated in emphysema were measured by tandem mass spectrometry and levels were normalized for lipid phosphorus (Pi) content.

Horizontal lines represents median and whiskers depict the $5^{th}$ and $95^{th}$ percentile. Groups were compared by ANOVA; *p=0.01 vs control; **P=<0.006 vs. control and vs. control+ cigarette smoke. H&E staining showed increased inflammatory cells in CS-exposed mice which is further aggravated in Tg mice exposed to CS. These data provide evidence for the hypothesis that EMAP II may be a predictor and mediator of emphysema formation.

EXAMPLE 16

Figure 18:
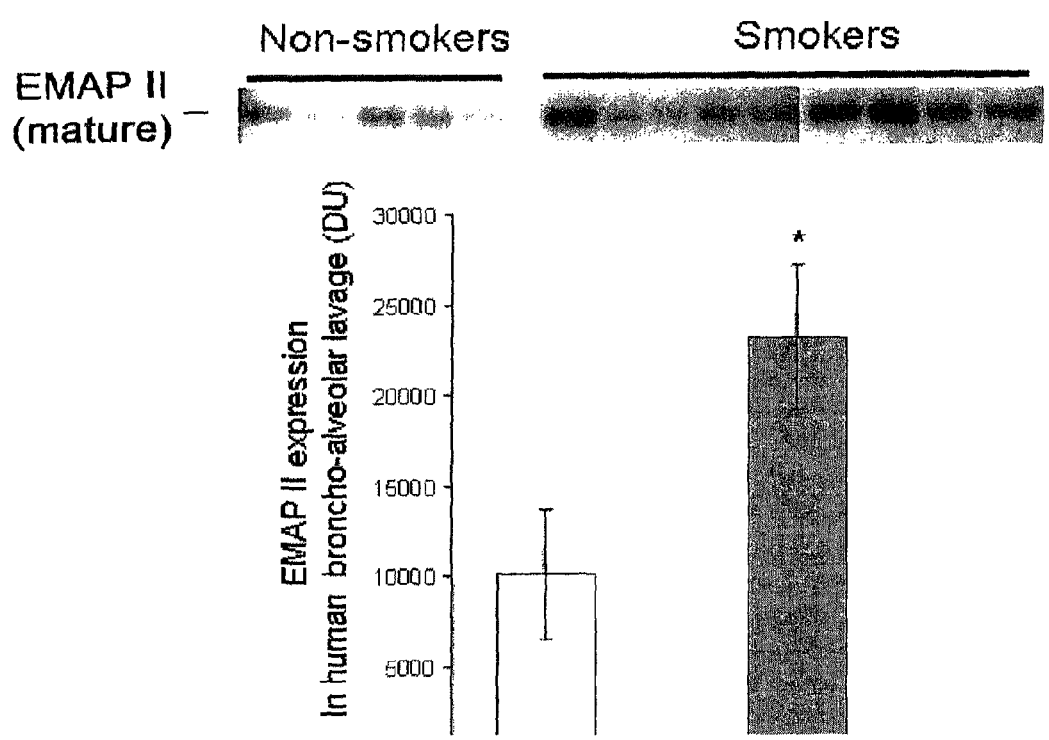
FIG. 18 shows secreted EMAP II (mature form) expression in the bronchoalveolar lavage (BAL) acellular fluid of smokers compared to non-smokers.

EMAP II Elevations in Human Lungs with COPD and in the Bronchoalveolar Lavage of Smokers To investigate the relevance of increased lung EMAP II levels for human emphysema, EMAP II in subjects diagnosed with emphysema was assessed. Immunostaining (IHC) of lung samples obtained from patients with emphysema at the time of lung transplantation with specific EMAP II antibody demonstrated markedly increased EMAP II staining compared with non-diseased lungs. Interestingly, variable levels of EMAP II expression were noted in individuals without a diagnosis of COPD at the time of tissue sampling. This variability may be related to smoking status, as the bronchoalveolar lavage obtained from active smokers without a COPD diagnosis exhibited increased EMAP II levels compared to nonsmokers (FIG. 18). Secreted EMAP II (mature form) expression in the bronchoalveolar lavage (BAL) acellular fluid of smokers was compared to non-smokers, as measured by western blotting with a specific EMAP II antibody. Levels measured by densitometry of EMAP II expression in individual BAL samples. (Mean±SEM,*p=<0.01).

It should be understood, of course, that the foregoing relates to exemplary embodiments of the invention and that modifications may be made without departing from the spirit and scope of the invention as set forth in the following claims.

We claim:
1. A method of treating a patient, comprising the step of:
    identifying a patient, wherein the patient is diagnosed with a disease selected from the group of diseases consisting of: emphysema and COPD;
    providing at least one compound that reduces EMAP II activity; and
    administering a therapeutically effective dose of said compound that reduces EMAP II activity in the patient;
    wherein said compound that reduces EMAP II activity is the rat monoclonal neutralizing antibody M7.

* * * * *